United States Patent [19]

Blaschke et al.

[11] Patent Number: 5,034,391
[45] Date of Patent: Jul. 23, 1991

[54] PIPERAZINYLALKYL-3(2H)-PYRIDAZI-NONES AND THE USE THEREOF AS AGENTS LOWERING BLOOD PRESSURE

[75] Inventors: Heinz Blaschke, Linz; Heimo Stroissnig, Vienna; Harald Fellier, Puchenau; Rita Enzenhofer, Ottensheim, all of Austria

[73] Assignee: CL Pharma Aktiengesellschaft, Linz, Austria

[21] Appl. No.: 443,166

[22] Filed: Nov. 30, 1989

[30] Foreign Application Priority Data

Dec. 6, 1988 [AT] Austria .................. 2991/88

[51] Int. Cl.$^5$ ............ A61K 31/50; C07D 237/14
[52] U.S. Cl. ..................... 514/252; 514/236.5; 544/120; 544/238
[58] Field of Search .......... 514/252, 236.5; 544/238, 120

[56] References Cited

U.S. PATENT DOCUMENTS

| | | | |
|---|---|---|---|
| 3,398,151 | 8/1968 | Wu | 544/230 |
| 4,067,982 | 1/1978 | Klemm et al. | 514/252 |
| 4,131,678 | 12/1978 | Amschlr et al. | 514/252 |
| 4,826,845 | 5/1989 | Kasztriner et al. | 514/236.5 |
| 4,859,672 | 8/1989 | Spada et al. | 544/238 |
| 4,910,201 | 5/1990 | Kawamura | 514/252 |

FOREIGN PATENT DOCUMENTS 1086238  1/1961  Fed. Rep. of Germany.
2261756  9/1975  France.
57-42679  3/1982  Japan.

OTHER PUBLICATIONS

Schoenbeck et al., "Monatsh. Chem.", vol. 99, 15-84 (1968).
Houben-Weyl, "Methoden der Org. Chem.", vol. XI, 1, 24-108 and 272-289, Georg Thieme Verlag, Stuttgart (1957).
Mizzoni et al., J.A.C.S., vol. 76, 2201 (1954).

*Primary Examiner*—Donald G. Daus
*Attorney, Agent, or Firm*—Wenderoth, Lind & Ponack

[57] ABSTRACT

The invention relates to new piperazinylalkyl-3(2H)-pyridazinones of the formula

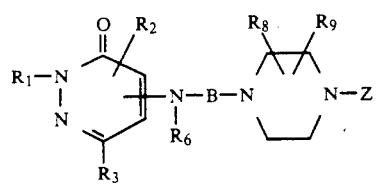

in which the radicals $R_1$ represents hydrogen, phenyl, benzyl, or ($C_1$-$C_6$)-alkyl which is unsubstituted or substituted one or more times by hydroxyl, piperidine, morpholine or by a group $NR_4R_5$ in which $R_4$ and $R_5$ can be identical or different and which represent hydrogen, methyl or ethyl, $R_2$ and $R_3$ represent hydrogen, halogen, ($C_1$-$C_6$)-alkoxy or ($C_1$-$C_6$)-alkyl, where at least one of the radicals $R_2$ or $R_3$ denotes hydrogen, $R_6$ represents hydrogen, ($C_1$-$C_4$)-alkyl, phenyl, benzyl or phenylethyl, B represents ($C_1$-$C_7$)-alkylene which is unsubstituted or substituted one or more times by hydroxyl, ($C_1$-$C_4$)-alkyl or by the group $NR_4R_5$ and which can optionally be closed to form an alicyclic 4- to 7-membered ring, $R_8$ and $R_9$, which can be identical or different, represent hydrogen or ($C_1$-$C_6$)-alkyl and Z represents phenyl, naphthyl, pyridyl or thiazolyl, each of which can be unsubstituted or substituted one or more times by ($C_1$-$C_6$)-alkyl, ($C_1$-$C_6$)-alkoxy, benzyloxy, trifluoromethyl, halogen, nitro, ($C_3$-$C_7$)-cycloalkoxy, ($C_1$-$C_4$)-alkylthio, trifluoromethylthio or by the group $NR_4R_5$, the pharmaceutically utilizable salts thereof, a process for the preparation thereof and the use thereof as medicament for the treatment of hypertension, cardiac insufficiency and disturbances of peripheral circulation.

3 Claims, No Drawings

PIPERAZINYLALKYL-3(2H)-PYRIDAZINONES AND THE USE THEREOF AS AGENTS LOWERING BLOOD PRESSURE

The present invention relates to new piperazinylalkyl-3-(2H)-pyridazinones and the pharmaceutically utilizable salts thereof, process for the preparation thereof and the use thereof as agents lowering blood pressure.

It is known that α-receptor blockers can be used as agents lowering blood pressure. Thus, for example, U.S. Pat. No. 3,714,342 describes arylsubstituted piperazinyl-propyleneamino-uracils which act to lower blood pressure and block the raising effect on blood pressure caused in pithed rats by adrenaline and noradrenaline.

The invention relates to new piperazinylalkyl-3(2H)-pyridazinones of the formula

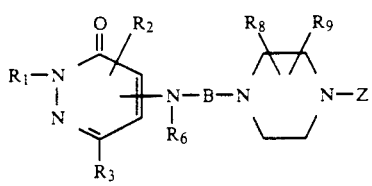

in which the radicals $R_1$ represents hydrogen, phenyl, benzyl, or $(C_1-C_6)$-alkyl which is unsubstituted or substituted one or more times by hydroxyl, piperidine, morpholine or by a group $NR_4R_5$ in which $R_4$ and $R_5$ can be identical or different and which represent hydrogen, methyl or ethyl, $R_2$ and $R_3$ represent hydrogen, halogen, $(C_1-C_6)$-alkoxy or $(C_1-C_6)$-alkyl, where at least one of the radicals $R_2$ or $R_3$ denotes hydrogen, $R_6$ represents hydrogen, $(C_1-C_4)$-alkyl, phenyl, benzyl or phenylethyl, B represents $(C_1-C_7)$-alkylene which is unsubstituted or substituted one or more times by hydroxyl, $(C_1-C_4)$-alkyl or by the group $NR_4R_5$ and which can optionally be closed to form an alicyclic 4- to 7-membered ring, $R_8$ and $R_9$, which can be identical or different, represent hydrogen or $(C_1-C_6)$-alkyl and Z represents phenyl, naphthyl, pyridyl or thiazolyl, each of which is unsubstituted or substituted one or more times by $(C_1-C_6)$-alkyl, $(C_1-C_6)$-alkoxy, benzyloxy, trifluoromethyl, halogen, nitro, $(C_3-C_7)$-cycloalkoxy, $(C_1-C_4)$-alkylthio, trifluoromethylthio or by the group $NR_4R_5$, the pharmaceutically utilizable salts thereof, a process for the preparation thereof and the use thereof as medicament for the treatment of hypertension, cardiac insufficiency and disturbances of peripheral circulation.

The term $(C_1-C_6)$-alkyl embraces all saturated hydrocarbon radicals which are straight-chain or branched one or more times and have 1 to 6 carbon atoms, such as, for example, methyl, isopropyl, tert. butyl, neopentyl, hexyl and the like. The alkyl radical in the $(C_1-C_6)$-alkoxy group has the above meaning. The term $(C_1-C_7)$-alkylene stands for a divalent saturated hydrocarbon radical which is straight-chain or branched one or more times and has 1 to 7 carbon atoms, it being possible if at least 4 carbon atoms are present for the alkylene chain optionally to be closed to form an alicyclic saturated ring with 4 to 7 carbon atoms, such as, for example, cyclobutylene, cycloheptylene. The cycloalkyl radical in the $(C_3-C_7)$-cycloalkoxy group has the meaning of a saturated alicyclic hydrocarbon radical with 3 to 7 carbon atoms. Halogen is defined as fluorine, chlorine, bromine or iodine.

The compounds of the formula 1 which are preferred are those in which the radicals $R_1$ represents hydrogen, methyl, ethyl, tert.-butyl, benzyl, 2-hydroxyethyl or 2-dimethylaminoethyl, $R_2$ and $R_3$ represent hydrogen, chlorine, bromine or methoxy, where at least one of the radicals $R_2$ or $R_3$ denotes hydrogen, $R_6$ represents hydrogen, methyl or ethyl, B represents straight-chain $(C_2-C_6)$-alkylene, $R_6$ and $R_9$ represent hydrogen and Z represents phenyl which is unsubstituted or substituted one or more times by methyl, $(C_1-C_3)$-alkoxy, benzyloxy, trifluoromethyl, fluorine, chlorine or nitro, or represents unsubstituted 2-pyridyl.

The compound 2-methyl-4-chloro-5-((2-(4-(2-methoxyphenyl)-1-piperazinyl)ethyl)amino)-3(2H)-pyridazinone is particularly preferred.

If $R_1$ has the meaning of hydrogen, the compounds of the formula I can be partially or entirely in their tautomeric form. The present invention also relates to these tautomeric forms.

The preparation of the compounds of the formula I and the salts thereof is such that a) a compound of the formula

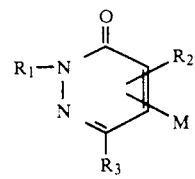

in which $R_1$, $R_2$ and $R_3$ are as defined above, and M denotes a leaving group, is reacted with a compound of the formula

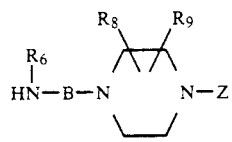

in which $R_6$, B, $R_8$, $R_9$ and Z are as defined above, or b) in a compound of the formula I in which one of the radicals $R_2$ or $R_3$ represents halogen, and the remaining radicals are as defined above, the halogen of $R_2$ or $R_3$ is replaced by hydrogen by means of hydrogenating dehalogenation, or c) a compound of the formula I in which one of the radicals $R_2$ or $R_3$ represents halogen, and the remaining radicals are as defined above, is reacted with an alkali metal alcoholate, whereupon the halogen of $R_2$ or $R_3$ is converted into a radical with the meaning $(C_1-C_6)$-alkoxy, or d) in a compound of the formula I in which $R_1$ has the meaning of i-propyl, sec. butyl, t-butyl or benzyl, and the remaining radicals are as defined above, $R_1$ is eliminated by acids or e) a pyridazine of the formula

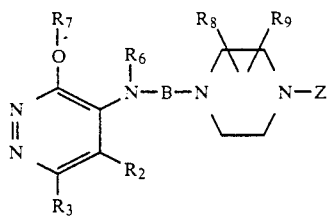

in which $R_2$, $R_3$, $R_6$, B, $R_8$, $R_9$ and Z are as defined above, and $R_7$ has the meaning of $(C_1-C_6)$-alkyl, is converted by ether cleavage with acid into the corresponding 3(2H)-pyridazinone or f) a compound of the formula I in which $R_1$ represents hydrogen and one of the radicals $R_2$ or $R_3$ represents halogen, and the remaining radicals are as defined above, is alkylated in position 2 of the pyridazine ring by reaction with an alkylating reagent and g) if desired a compound of the formula I which has been obtained as in a) to e) is converted into the pharmaceutically tolerated salts thereof. Suitable as leaving group M in process variant a) are all leaving groups customarily used, such as halogen, p-toluenesulphonyl, methanesulphonyl or trifluoromethanesulphonyl and the like. Compounds of the formula II in which M has the meaning of chlorine or bromine are preferably employed. The reaction in process variant a) is carried out in such a way that a compound of the formula II or a tautomer thereof is reacted with a compound of the formula III in a diluent which is inert under the reaction conditions at temperatures between about 20° and 150° C., or without solvent in the melt. Examples of suitable diluents are DMF, DMSO, acetonitrile, benzene, toluene, acetone, diethyl ketone, ethyl acetate, amyl acetate, ethylene glycol dimethyl ether, diethylene glycol dimethyl ether, tetralin or alcohols such as methanol, ethanol, hexanol, decanol, dioxane or tetrahydrofuran. The reaction takes between about 2 and 200 hours, the reaction times being shorter at higher reaction temperatures and vice versa. The preferred reaction conditions are the reaction of the reactants in acetonitrile for 5-50 hours with the addition of at least one mole of potassium bicarbonate as acid-binding agent at the reflux temperature. Reaction of a compound of the formula II with a compound of the formula III produces positional isomers because $R_2$ behaves like a leaving group. The positional isomers are separated by methods customary in chemistry, preferably by recrystallization and column chromatography.

In process variant b) the halogen of $R_2$ or $R_3$ is replaced by hydrogen by means of hydrogenating dehalogenation. It is preferably carried out in solution with the addition of a catalyst composed of noble metal or of Raney nickel. The use of palladium on charcoal as catalyst has proved particularly appropriate. Suitable solvents are alcohols such as methanol, ethanol, hexanol and the like, esters such as methyl acetate, ethyl acetate and the like, glacial acetic acid or aqueous hydrochloric acid or sodium hydroxide solution. The pressures customary for catalytic hydrogenation are used, preferably pressures from atmospheric pressure up to about 5 bar. The temperature can be between about 0° C. and 120° C., depending on the compound used and on the pressure; it is preferably 20°-70° C. Hydrogenation is carried out until the calculated stoichiometric amount of hydrogen has been taken up, a small excess of hydrogen not being disadvantageous in most cases.

In process variant c) the reaction with the alkali metal alcoholate, preferably sodium methylate, is carried out in a polar diluent such as DMF, DMSO, in cyclic ethers such as dioxane or tetrahydrofuran, in diethyl ether, diethylene glycol dimethyl ether or in alcohols, it being particularly preferable to use the alcohol on which the alcoholate is based. The reaction is carried out at temperatures from about 80° to 200° C. and can, if desired, be carried out in a pressurized vessel under pressures from about 2 to 10 bar. The reaction takes about 6 to 120 hours, depending on the nature of the starting compound and the reaction parameters, especially depending on the pressure and temperature. The reaction is preferably carried out under atmospheric pressure in methanolic solution at the reflux temperature for 30-60 hours.

The elimination of $R_1$ in process variant d) can be carried out using inorganic or organic acids. Examples of inorganic acids are HCl and HBr, it being possible to use these acids both in aqueous solution and dissolved in glacial acetic acid. Examples of organic acids are trifluoroacetic acid, trifluoromethanesulphonic acid and methanesulphonic acid. The elimination is carried out by heating in the said acids at temperatures from about 50° to 120° C., preferably at the reflux temperature; the reaction takes about 0.5 to 12 hours, depending on the nature of the starting compounds and the other reaction parameters.

The conversion of a pyridazine of the formula IV by ether cleavage into a 3(2H)-pyridazinone of the formula I in process variant e) can be carried out with the acids mentioned in process variant d). Compounds of the formula IV in which $R_7$ has the meaning of methyl are preferably employed. The reaction is carried out at about 50°-120° C., preferably at the reflux temperature of the acid employed, for from 5 minutes to 6 hours, depending on the nature of the starting compounds and the other reaction parameters.

The reaction in process variant f) of a compound of the formula I in which the radical $R_1$ represents hydrogen with an alkylating reagent is carried out in aqueous alkaline solution, it being possible to add as cosolvent alcohols such as methanol or ethanol, cyclic ethers, for example: THF, dioxane, DMF or DMSO. The reaction can be carried out at temperatures from about 20° to 120° C., preferably at 20° to 70° C. The reaction takes 1 to 12 hours, preferably 1-4 hours, depending on the nature of the starting compounds and the other reaction parameters.

The working up of the compounds obtained in process variants a) to f) is carried out in the customary way by evaporation, precipitation with water, precipitation as salt, recrystallization or by preparative column chromatography. The latter method is particularly important in the case where the substituent $R_2$ in process variant a) behaves like a leaving group under the given reaction conditions, which results in final products which are positional isomers.

The compounds of the formula I obtained in the reaction as in a) to f) are bases and can be converted in a customary manner into the pharmaceutically utilizable salts thereof with inorganic or organic acids. The salt formation can be carried out, for example, by dissolving a compound of the formula I in a suitable solvent such as, for example, in water, acetone or acetonitrile, in alcohols such as methanol, ethanol, hexanol, decanol or in mixtures of these alcohols with ethers, preferably with diethyl ether, adding at least the equivalent amount of the desired acid, ensuring that mixing is efficient and, after the salt formation is complete, filtering off the precipitated salt or removing the solvent by distillation in vacuo. The salts can be recrystallized, if necessary, after the isolation.

Examples of pharmaceutically utilizable salts are salts with inorganic acids such as, for example, hydrochloric acid, hydrobromic acid, sulphuric acid, phosphoric acid or nitric acid or with organic acids such as citric acid, tartaric acid, maleic acid, fumaric acid, succinic acid, maleic acid, methanesulphonic acid, aminosulphonic acid, acetic acid, benzoic acid and the like.

The pyridazones used as starting materials are known or can be prepared by methods known per se. Thus, 4,5-dichloro-3(2H)-pyridazinone and 4,5-dichloro-2-methyl-3(2H)-pyridazinone are obtained by condensation of mucochloric acid with hydrazine or methylhydrazine by the method of F. Reichenbacher and K. Drury, German Patent Specification 1,086,238, and 4,5-dichloro-2-hydroxyethyl-3(2H)-pyridazinone and 4,5-dichloro-2-diethylaminoethyl-3(2H)-pyridazinone are obtained as compound analogous to 4,5-dichloro-2-dimethyl-aminoethyl-3(2H)-pyridazinone in a reaction analogous to that of R. Schoenbeck and E. Kloimstein, Monatsh. Chem. 99, 15 (1968).

The piperazinylalkyl derivatives used as starting materials are known or can be prepared in analogy to known methods. Thus, 4-aryl- and 4-heteroaryl-piperazine derivatives which carry a cyanoalkyl radical in the 1 position can be reduced by catalytic hydrogenation to the desired aminoalkylpiperazine derivatives. The preparative methods to be used are described in, for example: Houben-Weyl, "Methoden der organischen Chemie" (Methods of Organic Chemistry) Vol. XI, 1, pages 24-108 and 272-289, Georg Thieme Verlag Stuttgart (1957), and in Jp. Kokai 82/42.679, U.S. Pat. No. 3,398,151, French Patent Specification 2,261,756 and U.S. Pat. No. 3,919,226. The pyridazines of the formula IV can be prepared by the method indicated in Example 14. 3,4,6-Dichloropyridazine is obtained by the method of R. H. Mazzoni and P. E. Spoerri, J.Am. Chem. Soc. 76, 2201 (1954).

The new compounds of the formula I and the pharmaceutically utilizable salts thereof show in in vitro models an excellent inhibition of the peripheral alpha receptors (alpha$_1$ adrenoceptors). In addition, many of the substances investigated have a good action on central 5HT-1A receptors.

By reason of these pharmacological properties, the new compounds can be used alone or mixed with other active substances in medicaments in the form of customary pharmaceutical formulations for high blood pressure and cardiac disorders.

The compounds of the formula I are intended for use in humans and can be administered in a customary manner, such as, for example, orally or parenterally. They are preferably administered orally, in which case the daily dose is about 0.015 to 15 mg/kg of body weight, preferably 0.15 to 1.5 mg/kg of body weight. The daily dose on intravenous administration is about 1.5 to 1500 mcg/kg of body weight, preferably about 15–150 mcg/kg of body weight. However, the treating physician can also prescribe doses above or below this, depending on the general condition and the age of the patient, the relevant substance of the formula I, the nature of the disease and the type of formulation.

The compounds of the formula I can be administered alone or in conjunction with other pharmaceutically active substances, with the content of the compounds of the formula I being between about 0.1 and 99%. In general, the pharmaceutically active compounds are in the form of a mixture with suitable inert auxiliaries and/or excipients or diluents, such as, for example pharmaceutically acceptable solvents, gelatin, gum arabic, lactose, starch, magnesium stearate, talc, vegetable oils, polyalkylene glycol, vaseline and the like. The pharmaceutical products can be in solid form, for example as tablets, coated tablets, suppositories, capsules and the like, in semisolid form, for example as ointments, or in liquid form, for example as solutions, suspensions or emulsions. Where appropriate they are sterilized and contain auxiliaries such as preservatives, stabilizers or emulsifiers, salts to alter the osmotic pressure and the like.

In particular, pharmaceutical products can contain the compounds according to the invention in combination with other substances of therapeutic value. The compounds according to the invention can be formulated with the latter, for example, together with the abovementioned auxiliaries and/or excipients or diluents to give combination products.

The compounds listed hereinafter as example are mainly in the form of their salts and/or solvates, the stated numbers indicating the particular stoichiometric ratio. In the UV spectrum, the first number denotes the frequency, and the number in brackets (second number) denotes the extinction.

Abbreviations used:
S: shoulder (in the UV spectrum)
m.p.: melting point
Cl (tot): chlorine (total)
eq.: equivalent
calc.: calculated
sbl.: sublimation

EXAMPLE 1

2-Methyl-5-bromo-4-((2-(4-(2-methoxyphenyl)-1-piperazinyl)ethyl)amino)-3(2H)-pyridazinone and 2-methyl-4-bromo-5-((2-(4-(2-methoxyphenyl)-1-piperazinyl)ethyl)amino)-3(2H)-pyridazinone 3.0 g (0.0112 mol) of 2-methyl-4,5-dibromo-3(2H)-pyridazinone, 2.64 g (0.0112 mol) of 1-(2-aminoethyl)-4-(2-methoxyphenyl)piperazine and 1.2 g (0.0112 mol) of finely powdered potassium bicarbonate are heated in 100 ml of dimethylformamide at 80° C. for 20 hours, while stirring vigorously; inorganic materials are then removed by hot filtration with suction, and the filtrate is concentrated with a vapour diffusion pump. The remaining brown oil is dissolved in 0.5N HCl, extracted 3 times with ether, the aqueous phase is made alkaline, and partitioning between water and chloroform is carried out. after the chloroform phase has been dried with sodium sulphate and concentrated, 4.74 g of brown oil remain, and this is fractionated on silica gel (Matrex silica Si60, 0.020–0.045 mm) by preparative column chromatography with methylene chloride/methanol 40:1.5. The first fraction contains 0.67 g of 2-methyl-5-bromo-4-((2-(4-(2-methoxyphenyl)-1-piperazinyl)ethyl)amino)-3(2H)-pyridazinone, 14.2% of theory; addition of the equivalent amount of fumaric acid in abs. ethanol results in the fumarate as a colourless crystalline substance of m.p. 185°–186° C.; C 49.5%, H 5.3%, Br 15.3%, N 12.6%, O 17.3%, UV in 0.1N HCl: 208(4.63), 226(S,4.40), 286(S,3.95), 302(4.07).

Further elution results in a second fraction containing 2.07 g of 2-methyl-4-bromo-5-((2-(4-(2-methoxyphenyl)-1-piperazinyl)ethyl)amino)-3(2H)-pyridazinone, which are dissolved in absolute ethanol, and fumaric acid is added. The colourless crystalline fumarate (2.3 eq.) of m.p. 125°–129° C. is obtained, 43.8% of theory; C 46.3%, H 5.0%, Br 11.9%, N 9.9%, O 26.9%, UV in 0.1N HCl: 212(4.63), 226(S,4.40), 282(S,3.83), 302 (S,3.71).

EXAMPLE 2

2-Methyl-5-chloro-4-((2-(4-(2-methoxyphenyl)-1-piperazinyl)ethyl)amino)-3(2H)-pyridazinone and 2-methyl-4-chloro-5-((2-(4-(2-methoxyphenyl)-1-piperazinyl)ethyl)amino)-3(2H)-pyridazinone 10.0 g (0.0559 mol) of 2-methyl-4,5-dichloro-3(2H)-pyridazinone, 13.2 g (0.0559 mol) of 1-(2-aminoethyl)-4-(2-methoxyphenyl)piperazine and 5.6 g (0.0559 mol) of potassium bicarbonate are heated under reflux in 200 ml of acetonitrile for 20 hours while stirring, inorganic materials are removed by hot filtration with suction, and the filtrate is cooled. 7.7 g of 2-methyl-5-chloro-4-((2-(4-(2-methoxyphenyl)-1-piperazinyl)ethyl)amino)-3(2H)-pyridazinone, 36.5% of theory, separate out as a colourless crystalline precipitate which provides 6.8 g (32.2%) of pure base after recrystallization from ethanol. Treatment with ethereal HCl in ethanol converts it into the dihydrochloride, m.p. 210°–220° C.; C 45.9%, H 5.7%, Cl(tot) 23.6%, Cl− 16.0%; colourless crystalline substance; UV in 0.1N HCl: 210(4.55), 230(4.30), 300(4.17). Cooling of the acetonitrile mother liquor results in a white crystalline precipitate of 4.5 g of 2-methyl-4-chloro-5-((2-(4-(2methoxyphenyl)-1-piperazinyl)ethyl)amino-3(2H)-pyridazinone, 21.3% of theory, which is converted into the dihydrochloride of m.p. 218°–225° C. by dissolving in isopropanol and addition of ethereal hydrochloric acid and is obtained pure by recrystallization from isopropanol, m.p. 223°–227° C., colourless crystals, 14.3% of theory; C 48.0%, H 5.7%, Cl(tot) 23.5%, Cl− 15.7%, N 15.0%, O 7.8%; UV in ethanol: 210(4.5), 230(4.57), 286(4.00), 304(S,3.81).

EXAMPLE 3

2-t-Butyl-4-chloro-5-((2-(3-(3-trifluoromethylphenyl)-1-piperazinyl)ethyl)amino)-3(2H)-pyridazinone and 2-t-butyl-5-chloro-4-((2-(3-(3-trifluoromethylphenyl)-1-piperazinyl)ethyl)amino)-3(2H)-pyridazinone 15.0 g (0.055 mol) of 1-aminoethyl-4-(3-trifluoromethylphenyl)piperazine and 15.2 g (0.069 mol) of 2-t-butyl-4,5-dichloro-3(2H)-pyridazinone are heated with 6.9 g (0.069 mol) of finely powdered potassium bicarbonate in 100 ml of acetonitrile with exclusion of moisture under reflux while stirring vigorously for 96 hours; solid material is removed by filtration, the filtrate is concentrated in vacuo, the residue is partitioned between ether and 1N HCl, the acid phase is extracted twice more with ether and is then made alkaline with sodium hydroxide solution and extracted anew with chloroform 3 times, and the organic phase is dried with sodium sulphate and the solvent is evaporated; the residue weighs 30.1 g and is subjected to preparative column chromatography on silica gel (Matrex silica Si60, 0.020–0.045 mm) with the eluent methylene chloride/methanol 40:1. 18.8 g of 2-t-butyl-4-chloro-5-((2-(3-(3-trifluoromethylphenyl)-1-piperazinyl)ethyl)amino)-3(2H)-pyridazinone are obtained as the first fraction; 74.6% of theory. 3.80 g of this are dissolved in 50 ml of acetone and converted with ethereal hydrochloric acid into 3.55 g of colourless crystalline hydrochloride (2.8 HCl eq.) which is readily soluble in water and has m.p. 124°–127° C.; 54.0% of theory; C 42.4%, H 6.0%, Cl(tot) 23.0%, Cl− 16.7%, F 9.2%, N 11.9%, O 7.5%; UV in ethanol: 206(4.39), 210(4,4), 216(4.37), 258(4.08), 304(4.12). The second fraction eluted is 8.3 g of isomeric 2-t-butyl-5-chloro-4-((2-(3-(3-trifluoromethylphenyl)-1-piperazinyl)ethyl)amino)-3(2H)-pyridazinone; 32.9% of theory; 1.50 g of this fraction in 50 ml of absolute ethanol are precipitated with an excess of ethereal hydrochloric acid and give 1.20 g of dihydrochloride of m.p. 187°–190° C. as a colourless crystalline substance which is readily soluble in water. 22.6% of theory; C 47.4%, H 5.5%, Cl(tot) 20.0%, Cl− 13.2%, F 10.3%, N 13.2%, O 3.6%; UV in ethanol: 212(S,4.39), 232(4.52), 256(4.19), 290(3.97), 304(S,3.86).

EXAMPLE 4

2-Methyl-4-chloro-5-((3-(4-(2-methoxyphenyl)-1-piperazinyl)propyl)amino)-3(2H)-pyridazinone and 2-methyl-5-chloro-4-((3-(4-(2-methoxyphenyl)-1-piperazinyl)propyl)amino)-3(2H)-pyridazinone 10.0 g (0.040 mol) of 1-aminopropyl-4-(2-methoxyphenyl)-piperazine and 7.9 g (0.044 mol) of 2-methyl-4,5-dichloro-3(2H)-pyridazinone are heated together with 4.4 g (0.044 mol) of potassium bicarbonate in 100 ml of freshly distilled dioxane at 80° C. for 10 hours and then stirred at room temperature for 3 days. Removal of the inorganic material by filtration is followed by concentration in vacuo, dissolution of the residue in aqueous hydrochloric acid and extraction several times with ether; the aqueous phase is made alkaline with sodium hydroxide solution and extracted by shaking 3 times with chloroform and, after drying with sodium sulphate and concentration in vacuo, 15.7 g of a mixture of isomers are obtained. Preparative column chromatography on silica gel (Matrex silica Si60 0.020–0.045 mm) with ether/methanol 40:5 as mobile phase is carried out. The first fraction eluted contains 7.43 g of 2-methyl-4-chloro-5-((3-(4-(2-methoxyphenyl)-1-piperazinyl)-propyl)amino)-3(2H)-pyridazinone, 47.5% of theory, 5.0 g of this were dissolved in absolute ethanol, and addition of ethanolic hydrochloric acid provided 5.6 g of dihydrochloride of m.p. 205°–220° C.; C 48.7%, H 6.5%, Cl(tot) 22.8%, Cl− 15.3%, N 15.0%, O 7.0%; UV in 0.1 N HCl: 210(4.49), 230(4.54), 282(3.93), 302(S,3.85). On continued elution, 5.95 g of 2-methyl-5-chloro-4-((3-(4-(2-methoxyphenyl)-1-piperazinyl)-propyl)amino)-3(2H)-pyridazinone, 38.1% of theory, are isolated as second fraction. After 4.0 g of this product had been dissolved in absolute ethanol, and ethanolic hydrochloric acid had been added, 3.9 g of dihydrochloride of m.p. 226°–228° C. were obtained; 37.1% of theory; C 49.0%, H 6.5%, Cl(tot) 22.9%, Cl− 15.3%, N 14.8%, O 6.8%; UV in 0.1N HCl: 204(4.48), 230(S4.54), 286(S,3.95), 302(3.85), 312(S,4.04).

EXAMPLE 5

2-Methyl-4-chloro-5-((6-(4-(2-methoxyphenyl)-1-piperazinyl)hexyl)amino)-3(2H)-pyridazinone and 2-methyl-5-chloro-4-((6-(4-(2-methoxyphenyl)-1-piperazinyl)hexyl)amino)-3(2H)-pyridazinone 5.8 g (0.020 mol) of 1-aminohexyl-4-(2-methoxyphenyl)-piperazine and 4.45 g (0.025 mol) of 2-methyl-4,5-dichloro-2-methyl-3(2H)-pyridazinone are heated with 2.50 g (0.025 mol) of finely powdered potassium bicarbonate in 100 ml of absolute ethanol with exclusion of moisture under reflux while stirring vigorously for 48 hours; the inorganic precipitate is removed by filtration, the filtrate is concentrated in vacuo and acidified with 1N HCl, and the acid aqueous phase is extracted 3 times with ether, then made alkaline with sodium hydroxide solution and extracted anew with chloroform 3 times, and the organic phase is dried with sodium sulphate and the solvent is evaporated in vacuo; the residue of 10.0 g is subjected to preparative column chromatography on silica gel (Waters Prep-Pak) with the eluent methylene chloride/methanol/conc. ammonia 40:1.50:0.1. The first fraction eluted is 3.70 g of 2-methyl-4-chloro-5-((6-(4-(2-methoxyphenyl)-1-piperazinyl)hexyl)amino)-3(2H)-pyridazinone; 42.6% of theory. 2.00 g of this are dissolved in 50 ml of analytical grade ethanol and converted with ethereal hydrochloric acid into 2.20 g of colourless dihydrochloride which is soluble in water and has m.p. 160°–175° C.; 38.0% of theory; C 50.3%, H 6.8%, Cl(tot) 19.4%, Cl− 13.1%, N 13.2%, O 10.3%; UV in ethanol: 212(4.46), 216(4.45,S), 234(4.50), 286(3.96), 304(3,87,S). The second fraction eluted is 4.1 g of isomeric 2-methyl-5-chloro-4-((6-(4-(2-methoxyphenyl)-1- piperazinyl)hexyl)amino)-3(2H)-pyridazinone; 47.2% of theory. 2.00 g of this fraction are dissolved in 50 ml of analytical grade ethanol and converted with ethereal hydrochloric acid into 1.5 g of colourless crystalline dihydrochloride which is soluble in water and has m.p. 153°–165° C.; 19.7% of theory; C 52.3%, H 6.8%, Cl(tot) 20.6%, Cl− 13.8%, N 13.9%, O 6.4%; UV in ethanol: 212(4.47), 216(4.44), 240(4.29), 302(4,14), 312(3.89,S).

EXAMPLE 6

2-Methyl-4-chloro-5-((4-(4-(2-methoxyphenyl)-1-piperazinyl)butyl)amino)-3(2H)-pyridazinone and 2-methyl-5-chloro-4-((4-(4-(2-methoxyphenyl)-1-piperazinyl)butyl)amino)-3(2H)-pyridazinone 10.0 g (0.038 mol) of 4-aminobutyl-2-methoxyphenyl-piperazine and 8.5 g (0.048 mol) of 2-methyl-4,5-dichloro-3(2H)-pyridazinone are dissolved together with 4.75 g (0.048 mol) of potassium bicarbonate in 70 ml of anhydrous dimethyl sulphoxide and kept at 80° C. for 15 hours; the mixture is diluted with 200 ml of water and extracted several times with chloroform. The organic phase is washed 3 times with water and subsequently extracted with 1N HCl. The aqueous phase is made alkaline and extracted by shaking with chloroform and, after drying with sodium sulphate and concentration in vacuo, 16.9 g of a mixture of products are obtained. Subsequent fractionation is carried out by preparative column chromatography on silica gel (Matrex silica Si60 0.020– 0.045 mm) with ether/methanol 40:5 as mobile phase. 5.50 g (35.7% of theory) of 2-methyl-5-chloro-4-((4-(4-(2-methoxyphenyl)-1-piperazinyl)butyl)amino)-3(2H)-pyridazinone are isolated as the first fraction, 30.1% of theory; it is dissolved in absolute ethanol, and addition of ethanolic hydrochloric acid provides the dihydrochloride of m.p. 205°–207° C.; C 50.1%, H 6.5%, Cl(tot) 21.5%, Cl− 14.5%, N 14.4%, O 7.0%; UV in ethanol: 206(4.43), 210(4.50), 244(4.15), 296(4.12), 312(4.09). The second fraction to appear on further elution is 8.40 g of 2-methyl-4-chloro-5-((4-(4-(2- methoxyphenyl)-1-piperazinyl)butyl)amino)-3(2H)-pyridazinone, 54.6% of theory, which, after dissolution in absolute ethanol and addition of ethanolic hydrochloric acid, provides colourless crystalline dihydrochloride of m.p. 183°–192° C.; C 50.10%, H 6.1%, Cl(tot) 21.8%, Cl− 14.9%, N 14.9%, O 7.0%; UV in ethanol: 210(4.41), 218(4.42), 232(4.46), 236(4.45), 286(3.96).

EXAMPLE 7

2-methyl-4-chloro-5-((2-(4-(2,6-dimethylphenyl)-1-piperazinyl)ethyl)amino)-3(2H)-pyridazinone and 2-methyl-5-chloro-4-((2-(4-(2,6-dimethylphenyl)-1-piperazinyl)ethyl)amino)-3(2H)-pyridazinone 9.2 g (0.039 mol) of 1-aminoethyl-4-(2,6-dimethylphenyl)-piperazine and 8.8 g (0.049 mol) of 2-methyl-4,5-dichloro-3(2H)-pyridazinone are heated together with 4.9 g (0.049 mol) of finely powdered potassium bicarbonate in 100 ml of toluene with exclusion of moisture under reflux while stirring vigorously for 20 hours; the mixture is filtered to remove inorganic material and is concentrated in vacuo, the residue is dissolved in 1N HCl, the aqueous phase is extracted 3 times with ether, then made alkaline and extracted anew with chloroform 3 times, the organic phase is dried with sodium sulphate, and the solvent is evaporated; the residue of 15.7 g is subjected to preparative column chromatography on silica gel (Waters PrepPak) with the eluent methylene chloride/methanol 40:1. 5.70 9 of 2-methyl-4-chloro-5-((2-(4-(2,6-dimethylphenyl)-1-piperazinyl)ethyl)amino)-3(2H)-pyridazinone, 32.6% of theory, are obtained as the first fraction; 3.80 g of this are dissolved in 50 ml of absolute ethanol and converted by addition of ethereal hydrochloric acid into 3.00 g of colourless crystalline dihydrochloride which is readily soluble in water and has m.p. 235°–242° C.; 32.6% of theory; C 50.7%, H 6.3%, Cl(tot) 23.2%, Cl− 15.4%, N 15.6%, O 4.2%; UV in ethanol: 220(4.40), 232(4.49), 290(3.85), 311(3.81). The second fraction obtained from the column is 7.40 g of 2-methyl-5-chloro-4-((2-(4-(2,6-dimethylphenyl)-1-piperazinyl)ethyl)amino)-3(2H)-pyridazinone, 42.3% of theory; 4.0 g are dissolved in 50 ml of absolute ethanol, precipitated with an excess of ethereal hydrochloric acid and give 2.40 g of colourless crystalline hydrochloride which is readily soluble in water and has m.p. 225°–232° C.; 24.9% of theory; C 55.5%, H 6.8%, Cl(tot) 17.3%, Cl− 6.6%, N 17.2%, O 3.2%; UV in ethanol: 212(4.35), 216(4.34), 233(4.11), 304(4.09), 312(4.03).

The following compounds are prepared in analogy to Examples 1–7 above:

5-Chloro-4-((2-(4-methoxyphenyl)piperazinyl-1)ethyl)amino)-3(2H)-pyridazinone

Salt: 2.75 HCl ; solvate: 1.25 H2O
M.p. 251-256 deg. C., recryst.: ethanol
Yield: 76.2%
C: calc.: 41.95, found: 41.8
H: calc.: 5.64, found: 5.2
Cl: calc.: 27.32, found: 26.6

Cl—: calc.: 20.03, found: 19.9
N: calc.: 14.39, found: 14.2
O: calc.: 9.68, found: 9.0
UV: solvent: ethanol, 214 (4.39),302 (3.91),312 (3.85)

2-Methyl-5-chloro-4-((2-(4-phenylpiperazinyl-1)ethyl)amino)-3(2H)-pyridazinone

Salt: 1.6 HCl; solvate: 0.1 H2O
M.p. 218–220 deg. C., recryst.: ethanol
Yield: 23.5%
C: calc.: 50.05, found: 50.0
H: calc.: 5.88, found: 6.1
Cl: calc.: 22.59, found: 22.5
Cl—: calc.: 13.9, found: 14.1
N: calc.: 17.17, found: 17.2
O: calc.: 4.31, found: 4.2
UV: solvent: 0.1N HCl, 204 (4.48),232 (4.24),300 (4.11)

2-Methyl-5-chloro-4-(methyl-(2-(2-methoxyphenyl) piperazinyl-1) ethyl)amino)-3(2H)-pyridazinone Salt: 2.0 HCl; solvate: 0.5 H2O
M.p.: 224–231 deg. C., recryst.: ethanol
Yield: 41.1%
C: calc.: 48.16, found: 48.6
H: calc.: 6.17, found: 6.1
Cl: calc.: 22.45, found: 22.3
Cl—: calc.: 14.96, found: 15.1
N: calc.: 14.78, found: 14.6
O: calc.: 8.44, found: 8.4
UV: solvent:0.1N HCl, 210 (4.36),218 (4.36),236 (4.37),280 (s,3.95),300 (4.03)

2-Methyl-5-chloro-4-((2-(4-(2-methoxy-5-methylphenyl) piperazinyl-1)ethyl)amino)-3(2H)-pyridazinone Salt: 1.5 fumarate;
M.p.: 140–144 deg. C., recryst.: acetone
Yield: 25.5%
C: calc.: 53.05, found: 53.5
H: calc.: 5.70, found: 6.0
Cl: calc.: 6.26, found: 6.5
N: calc.: 12.37, found: 12.6
O: calc.: 22.61, found: 22.4
UV: solvent: 0.1N HCl, 206 (4.44),226 (4.27),298 (4.08),310 (s,4.02)

2-Methyl-5-chloro-4-((2-(4-(2-methoxy-4-methylphenyl) piperazinyl-1)ethyl)amino)-3(2H)-pyridazinone Salt: 1.5 fumarate;
M.p.: 151–154 deg. C., recryst.: acetone
Yield: 27.6%
C: calc.: 53.05, found: 53.0
H: calc.: 5.70, found: 5.9
Cl: calc.: 6.26, found: 5.8
N: calc.: 12.37, found: 12.2
O: calc.: 22.61, found: 23.1
UV: solvent: 0.1N HCl, 204 (4.51)226 (s,4.22),300 (4.47)

2-Methyl-5-chloro-4-((2-(4-(3-methoxyphenyl)piperazinyl-1) ethyl)amino)-3(2H)-pyridazinone Salt: 2.0 HCl;
M.p.: 161–169 deg. C., purif. by chromatography
Yield: 31.5%
C: calc.: 47.96, found: 47.9
H: calc.: 5.80, found: 5.9
Cl: calc.: 23.59, found: 23.5
Cl—: calc.: 15.73, found: 15.5
N: calc.: 15.54, found: 15.5
O: calc.: 7.10, found: 7.2
UV: solvent: ethanol, 214 (4.48),248 (s,4.06),304 (4.18),312 (s,4.1)

2-Methyl-5-chloro-4-((2-(4-(2-benzyloxyphenyl)-piperazinyl-1) ethyl)amino)-3(2H)-pyridazinone Salt: 2.0 HCl; solvate: 1.0 H2O
M.p.: 126–139 deg. C.,
Yield: 51.5% (crude mat.), 19.% (purif.mat.)
C: calc.: 53.20, found: 53.4
H: calc.: 5.39, found: 5.7
Cl: calc.: 19.63, found: 19.2
Cl—: calc.: 13.09, found: 12.8
N: calc.: 12.92, found: 12.7
O: calc.: 8.89, found: 9.0
UV: solvent: 1N HCl, 210 (4.58),234 (s,4.18),300 (4.08),311 (s,3.99)

2-Methyl-4-chloro-5-((2-(4-(2-hydroxyphenyl)piperazinyl-1) ethyl)amino)-3(2H)-pyridazinone Salt: 2.0 HBr; solvate: 1.5 H2O
M.p.: 208–213. deg. C.,
Yield: 17.6%
C: calc.: 37.06, found: 36.9
H: calc.: 4.94, found: 4.5
Cl: calc.: 6.44, found: 6.0
N: calc.: 12.71, found: 12.6
O: calc.: 10.16, found: 10.6
Br: calc.: 29.01, found: 29.4
UV: solvent: 1N HCl, 206 (4.55),230 (s,4.17),235 (s,4.10),300 (4.10),311 (s,4.02)

2-Methyl-5-chloro-4-((2-(4-(2-methylphenyl)piperazinyl-1) ethyl)amino)-3(2H)-pyridazinone Salt: 1.0 fumarate; solvate: 0.5 H2O
M.p.: 185–187 deg. C., recryst.: ethanol
Yield: 23.5%
C: calc.: 54.26, found: 53.9
H: calc.: 6.00, found: 6.0
Cl: calc.: 7.28, found: 7.7
N: calc.: 14.38, found: 14.3
O: calc.: 18.07, found: 18.1
UV: solvent: 0.1N HCl, 208 (4.43),230 (4.20),300 (4.10),312 (s,4.00)

2-Methyl-5-chloro-4-((2-(4-(3-trifluoromethylphenyl) piperazinyl-1)ethyl)amino-3(2H)-pyridazinone Salt: 1.15 HCl; solvate: 0.5 H2O
M.p.: 175–197 deg. C., recryst.: ethanol
Yield: 26.8%
C: calc.: 46.32, found: 46.7
H: calc.: 5.00, found: 5.0
Cl: calc.: 16.33, found: 16.5
Cl—: calc.: 8.73, found: 8.5
N: calc.: 15.00, found: 15.1
O: calc.: 5.14, found: 5.1
F: calc.: 12.21, found: 11.6
UV: solvent: ethanol, 208 (4.49),219 (s,4.37),238 (4.06),256 (4.16),304 (4.17)

2-Methyl-5-chloro-4-((2-(4-(4-chloro-3-trifluoromethylphenyl) piperazinyl-1)ethyl)amino)-3(2H)-pyridazinone Salt: 2.0 HCl; solvate: 0.2 H2O
M.p.: 185–188 deg. C., precipitn.: ethanol, diethyl ether
Yield: 25.6% (crude mat.), 22.1% (purif.mat.)
C: calc.: 41.04, found: 41.6

H: calc.: 4.29, found: 4.3
Cl: calc.: 26.92, found: 26.8
Cl—: calc.: 13.5, found: 13.5
N: calc.: 13.29, found: 13.3
O: calc.: 3.64, found: 3.7
F: calc.: 10.82, found: 10.3

2-Methyl-5-chloro-4-((2-(4-(3-chlorophenyl)piperazinyl-1)ethyl) amino)-3(2H)-pyridazinone Salt: 2.0 HCl; solvate: 0.15 H2O
M.p.: 195 deg. C (subl.), purif. by chromatography
Yield: 32.9%
C: calc.: 44.59, found: 44.7
H: calc.: 5.13, found: 5.2
Cl: calc.: 30.97, found: 30.6
Cl—: calc.: 15.48, found: 15.4
N: calc.: 15.29, found: 15.5
O: calc.: 5.15, found: 5.1
UV: solvent: ethanol, 210 (4.39),216 (4.40),235 (s,4.04),258 (4.13),304 (4.15)

2-Methyl-4-chloro-5-((2-(4-(3,5-dichlorophenyl)-piperazinyl-1) ethyl)amino)-3(2H)-pyridazinone Salt: 1.0 HCl;
M.p.: 191–201 deg. C., precipitn.: ethanol, diethyl ether
Yield: 42.6%
C: calc.: 45.05, found: 45.3
H: calc.: 4.67, found: 4.7
Cl: calc.: 31.29, found: 31.0
Cl—: calc.: 7.82, found: 7.8
N: calc.: 15.45, found: 15.3
O: calc.: 3.53, found: 3.2

2-Methyl-5-chloro-4-((2-(4-(2-fluorophenyl)piperazinyl-1) ethyl)amino-3(2H)-pyridazinone Salt: 1 HBr
M.p.: 210–214 deg. C., recryst.: ethanol
Yield: 34.1%
C: calc.: 45.70, found: 45.9
H: calc.: 4.96, found: 4.8
Cl: calc.: 7.94, found: 8.1
N: calc.: 15.68, found: 15.5
O: calc.: 3.58, found: 3.6
F: calc.: 4.25, found: 3.9
Br—: calc.: 17.89, found: 18.2
UV: solvent: 0.1N HCl, 208 (4.24),230 (4.28),300 (4.08),312 (s,3.98)

2-Methyl-5-chloro-4-((2-(4-(4-fluorophenyl)piperazinyl-1) ethyl)amino)-3(2H)-pyridazinone Salt: 2.0 HCl; solvate: 0.2 H2O
M.p.: 189–195 deg. C., recryst.: ethanol
Yield: 15.8%
C: calc.: 46.16, found: 46.6
H: calc.: 5.33, found: 5.3
Cl: calc.: 24.04, found: 24.0
Cl—: calc.: 16.03, found: 16.2
N: calc.: 15.83, found: 15.8
O: calc.: 4.34, found: 4.6
F: calc.: 4.29, found: 4.6
UV: solvent: ethanol, 206 (4.32),240 (4.27),304 (4.12),312 (s,4.08), 2-Methyl-5-chloro-4-((2-(4-(4-nitrophenyl)piperazinyl-1) ethyl)amino)-3(2H)-pyridazinone Salt: 0.9 HCl;
M.p.: 237–240 deg. C; recryst.: ethanol
Yield: 17.9%
C: calc.: 47.97, found: 48.2
H: calc.: 5.19, found: 5.2
Cl: calc.: 15.82, found: 16.0
Cl—: calc.: 7.50, found: 7.6
N: calc.: 19.74, found: 19.8
O: calc.: 11.28, found: 10.8
UV: solvent: ethanol, 204 (4.34),232 (4.18),304 (4.09),312 (s,4.06),382 (4.20)

2-t-Butyl-5-chloro-4-((2-(4-(2-methoxyphenyl)piperazinyl-1) ethyl)amino)-3(2H)-pyridazinone Salt: 1.5 fumarate;
M.p.: 162–165 deg. C., precipitn.: methanol, acetone
Yield: 14.%
C: calc.: 54.59, found: 54.5
H: calc.: 6.11, found: 6.3
Cl: calc.: 5.97, found: 6.1
N: calc.: 11.79, found: 11.7
O: calc.: 21.55, found: 21.3
UV: solvent: 0.1N HCl, 208 (4.65),282 (s,3.94),300 (4.01)

2-(2-Dimethylaminoethyl)-5-chloro-4-((2-(4-(2-methoxyphenyl) piperazinyl-1)ethyl)amino)-3(2H)-pyridazinone Salt: 2.95 HBr; solvate: 3.0 H2O
M.p.: 168–178 deg. C., recryst.: ethanol
Yield: 26.1%
C: calc.: 34.65, found: 34.8
H: calc.: 5.53, found: 5.3
N: calc.: 11.55, found: 11.5
O: calc.: 10.99, found: 10.9
Br—: calc.: 32.39, found: 32.5
UV: solvent: 0.1N HCl, 206 (4.42),230 (4.12),285 (3.79),302 (4.04),312 (3.86)

2-Hydroxyethyl-5-chloro-4-((2-(4-(2-methoxyphenyl) piperazinyl-1)ethyl)amino)-3(2H)-pyridazinone Salt: 2.0 HCl; solvate: 0.45 H2O
M.p.: 171–181 deg. C., recryst.: acetone
Yield: 25.6%
C: calc.: 46.68, found: 46.4
H: calc.: 5.96, found: 5.8
Cl: calc.: 21.75, found: 21.7
Cl—: calc.: 14.50, found: 14.5
N: calc.: 14.32, found: 14.1
O: calc.: 11.29, found: 11.0
UV: solvent: 0.1N HCl, 208 (4.52),232 (s,4.14),304 (4.10)

2-(2-Hydroxethyl)-5-chloro-4-((2-(4-(3-trifluoromethyl) piperazinyl-1)ethyl)amino)-3(2H)-pyridazinone Salt: 2.0 HCl; solvate: 0.85 H2O
M.p.: 113—120 deg. C; recryst.: acetone
Yield: 6.9%
C: calc.: 42.73, found: 43.3
H: calc.: 5.04, found: 5.0
Cl: calc.: 19.91, found: 19.4
Cl—: calc.: 13.28, found: 12.9
N: calc.: 13.11, found: 13.1
O: calc.: 8.39, found: 8.5
F: calc.: 10.67, found: 10.7
UV: solvent: ethanol, 206 (4.41),240 (4.09),258 (4.17),304 (4.18),312 (s,4.11)

2-Methyl-5-chloro-4-((2-(4-(pyridyl-2)piperazinyl-1)ethyl) amino)-3(2H)-pyridazinone Salt: 2.0 HCl; solvate: 0.45 H2O
M.p.: 200–210 deg. C., recryst.: ethanol
Yield: 19.5%
C: calc.: 44.71, found: 44.6
H: calc.: 5.60, found: 5.5
Cl: calc.: 24.74, found: 24.9
Cl—: calc.: 16.49, found: 16.7
N: calc.: 19.55, found: 19.6
O: calc.: 5.40, found: 5.4

2-Methyl-5-chloro-4-(methyl-(3-(4-(2-methoxyphenyl) piperazinyl-1)propyl)amino)-3(2H)-pyridazinone Salt: 1.0 fumarate; solvate: 1.0 H2O
M.p.: 159–165 deg. C., recryst.: ethanol
Yield: 40.8%
C: calc.: 52.98, found: 52.8
H: calc.: 7.04, found: 6.4
Cl: calc.: 6.52, found: 6.4
N: calc.: 12.87, found: 13.0
O: calc.: 20.58, found: 21.5

2-Methyl-5-chloro-4-((3-(4-(2-hydroxy-4-methylphenyl) piperazinyl-1)propyl)amino)-3(2H)-pyridazinone Salt: 1.0 fumarate;
M.p.: 193–197 deg. C., recryst.: ethanol
Yield: 34.3%
C: calc.: 54.38, found: 54.5
H: calc.: 5.95, found: 6.1
Cl: calc.: 7., found: 7.2
N: calc.: 13.79, found: 13.7
O: calc.: 18.9, fOund: 18.5

2-Methyl-5-chloro-4-((3-(4-(2-ethoxy-4-methylphenyl) piperazinyl-1)propyl)amino)-3(2H)-pyridazinone Salt: 2.0 HCl;
M.p.: 220–223 deg. C.,
Yield: 39.%
H: calc.: 6.54, found: 6.5
Cl: calc.: 21.58, found: 21.4
Cl—: calc.: 14.39, found: 14.4
N: calc.: 14.21, found: 14.4
O: calc.: 6.49, found: 6.9
UV: solvent: 0.1N HCl, 206 (4.45),226 (s,4.16),302 (4.10),312 (s,4.02), 2-Methyl-5-chloro-4-((3-(4-(2-methylphenyl)piperazinyl-1) piperazinyl-1)propyl)amino)-3(2H)-pyridazinone Salt: 1.0 fumarate;
M.p.: 184–186 deg. C.,
Yield: 30.%
C: calc.: 56.15, found: 55.6
H: calc.: 6.15, found: 6.2
Cl: calc.: 7.21, found: 7.3
N: calc.: 14.24, found: 14.4
O: calc.: 16.26, found: 16.5
UV: solvent: 0.1N HCl, 206 (4.42),230 (4.14),302 (4.08),312 (s,3.99)

2-Methyl-5-chloro-4-((3-(4-(2-fluorophenyl)piperazinyl-1) propyl)amino)-3(2H)-pyridazinone Salt: 1.0 fumarate;
M.p.: 161–163 deg. C., recryst.: ethanol
Yield: 28.3%
C: calc.: 53.28, found: 53.3
H: calc.: 5.49, found: 5.5
Cl: calc.: 7.15, found: 7.1
N: calc.: 14.12, found: 13.8
O: calc.: 16.13, found: 16.6
F: calc.: 3.83, found: 3.7
UV: solvent: 0.1N HCl, 204 (4.4),230 (4.24),302 (4.11),313 (s,4.17)

2-Methyl-5-chloro-4-((3-(4-(4-fluorophenyl))piperazinyl-1) propyl)amino)-3(2H)-pyridazinone Salt: 2.0 HCl ; solvate: 3.0 H2O
M.p.: 216 deg. C (subl.), reoryst.: ethanol
Yield: 22.5%
C: calc.: 42.66, found: 42.2
H: calc.: 6.17, found: 6.0
Cl: calc.: 20.98, found: 21.3
Cl—: calc.: 13.99, found: 14.0
N: calc.: 13.82, found: 14.2
O: calc.: 12.63, found: 12.8
F: calc.: 3.75, found: 3.5

2-Methyl-5-chloro-4-((2-(4-(pyridyl-2)piperazinyl-1)ethyl) amino)-3(2H)-pyridazinone Salt: 2.0 HCl; solvate: 0.15 H2O
M.p.: 219–226 deg. C., recryst.: ethanol
Yield: 14.4%
C: calc.: 46.57, found: 46.5
H: calc.: 5.87, found: 5.8
Cl: calc.: 24.26, found: 24.3
Cl—: calc.: 16.17, found: 16.2
N: calc.: 19.17, found: 19.2
O: calc.: 4.20, found: 4.2
UV: solvent: ethanol, 206 (4.24),250 (4.26),304 (4.24)

4-Chloro-5-((2-(4-(3-trifluoromethyl)piperazinyl-1)ethyl) amino)-3(2H)-pyridazinone Salt: 2.0 HCl; solvate: 2.0 H2O
M.p.: 173–176 deg. C; recryst.: ethanol
Yield: 60.3%
C: calc.: 39.98, found: 40.3
H: calc.: 4.93, found: 4.2
Cl: calc.: 20.82, found: 21.0
Cl—: calc.: 13.88, found: 14.1
N: calc.: 13.71, found: 13.9
O: calc.: 9.40, found: 9.5
F: calc.: 11.16, found: 11.1

2-Methyl-4-chloro-5-((2-(4-phenylpiperazinyl-1)ethyl)amino)-3(2H)-pyridazinone

Salt: 1.85 HCl; solvate: 0.7 H2O
M.p.: 171–180 deg. C., recryst.: ethanol
Yield: 39.%
C: calc.: 47.72, found: 48.2
H: calc.: 6.00, found: 6.3
Cl: calc.: 23.61, found: 23.2
Cl—: calc.: 15.33, found: 15.0
N: calc.: 16.37, found: 16.1
O: calc.: 6.36, found: 6.2
UV: solvent: 0.1N HCl, 206 (4.41),230 (4.57),288 (3.92)

2-Methyl-4-chloro-5-((2-(4-(2-methoxy-4-methylphenyl) piperazinyl-1)ethyl)amino)-3(2H)-pyridazinone Salt: 1.75 fumarate;
M.p.: 103–105 deg. C., recryst.: acetone
Yield: 37.6%
C: calc.: 52.48, found: 52.3
H: calc.: 5.59, found: 6.1
Cl: calc.: 5.96, found: 5.9
N: calc.: 11.77, found: 12.0

O: calc.: 24.20, found: 23.7
UV: solvent: 0.1N HCl, 210 (4.49),228 (4.57),282 (3.99),304 (s,3.81)

2-Methyl-4-chloro-5-((2-(4-(2-methoxy-5-methylphenyl) piperazinyl-1)ethyl)amino)-3(2H)-pyridazinone Salt: 1.25 fumarate;
M.p.: 80–83 deg. C., recryst.: acetone
Yield: 27.3%
C: calc.: 53.68, found: 53.6
H: calc.: 5.82, found: 6.3
Cl: calc.: 6.60, found: 6.6
N: calc.: 13.04, found: 13.4
O: calc.: 20.85, found: 20.1
UV: solvent: 0.1N HCl, 212 (4.52),228 (4.58),286 (4.03),304 (s,3.80)

2-Methyl-4-chloro-5-(ethyl-(2-(4-(2-methoxyphenyl) piperazinyl-1)ethyl)amino)-3(2H)-pyridazinone Salt: 2.0 HCl
M.p.: 178–183 deg. C., recryst.: ethanol
Yield: 31.9% (crude mat.), 22.5% (purif.mat.)
C: calc.: 50.17, found: 50.4
H: calc.: 6.32, found: 6.3
Cl: calc.: 22.21, found: 22.0
Cl—: calc.: 14.81, found: 14.7
N: calc.: 14.63, found: 14.8
O: calc.: 6.68, found: 6.5

2-Methyl-4-chloro-5-((2-(4-(3-methoxyphenyl)piperazinyl-1) ethyl)amino)-3(2H)-pyridazinone Salt: 2.0 HCl; solvate: 0.2 H2O
M.p.: 170–174 deg. C., precipitn.: ethanol, diethyl ether
Yield: 47.%
C: calc.: 47.58, found: 47.6
H: calc.: 5.86, found: 6.1
Cl: calc.: 23.41, found: 22.9
Cl—: calc.: 15.6, found: 15.1
N: calc.: 15.41, found: 15.2
O: calc.: 7.75, found: 7.6
UV: solvent: ethanol, 214 (4.6),232 (4.56),250 (s,4.09),290 (3.97),304 (s,3.89)

2-Methyl-4-chloro-5-((2-(4-(2-ethoxyphenyl)piperazinyl-1) ethyl)amino)-3(2H)-pyridazinone Salt: 1.0 fumarate;
M.p.. 197–199 deg. C., recryst.: acetone
Yield: 35.2%
C: calc.: 54.38, found: 54.2
H: calc.: 5.95, found: 6.0
Cl: calc.: 6.98, found: 6.9
N: calc.: 13.79, found: 13.6
O: calc.: 18.90, found: 19.3

2-Methyl-4-chloro-5-((2-(4-(2-hydroxyphenyl)piperazinyl-1) ethyl)amino)-3(2H)-pyridazinone Salt: 2.25 HBr; solvate: 1.33 H2O
M.p.: 191–195 deg. C.,
Yield: 22.6%
C: calc.: 35.82, found: 35.9
H: calc.: 4.76, found: 4.6
Cl: calc.: 6.22, found: 6.1
N: calc.: 12.29, found: 11.8
O: calc.: 9.36, found: 11.6
Br—: calc.: 31.54, found: 30.0
UV: solvent: 1N HCl, 208 (4.54),230 (4.53),282 (3.96),302 (s,3.8)

2-Methyl-4-chloro-5-((4-(2-hydroxy-4-methylphenyl)-piperazinyl -1)ethyl)amino)-3(2H)-pyridazinone Salt: 2.75 HCl; solvate: 3.25 H2O
M.p.: 157–167 deg. C., recryst.: ethanol
Yield: 78.9%
C: calc.: 40.28, found: 40.8
H: calc.: 6.24, found: 5.9
Cl: calc.: 24.77, found: 24.5
Cl—: calc.: 18.17, found: 17.9
N: calc.: 13.05, found: 12.8
O: calc.: 15.65, found: 16.0
UV: solvent: ethanol, 214 (4.80),230 (4.88),286 (4.30),305 (s,4.09)

2-Methyl-4-chloro-5-((2-(4-(2-benzyloxyphenyl)-piperazinyl-1) ethyl)amino)-3(2H)-pyridazinone Salt: 1.8 HCl; solvate: 1.5 H2O
M.p.: 154–159 deg. C., recryst.: ethanol
Yield: 49.1% (crude mat.), 25.2% (purif.mat.)
C: calc.: 46.22, found: 46.2
H: calc.: 4.82, found: 5.3
Cl: calc.: 5.68, found: 5.1
N: calc.: 11.23, found: 10.6
O: calc.: 8.98, found: 8.9
Br—: calc.: 23.06, found: 23.9
UV: solvent: 0.1N HCl, 208 (4.67),230 (4.54),284 (3.96),304 (s,3.82)

2-Methyl-4-chloro-5-((2-(4-(2-methylphenyl)piperazinyl-1) ethyl)amino)-3(2H)-pyridazinone Salt: 2.0 fumarate; solvate: 2.75 H2O
M.p.: 149–155 deg. C., recryst.: ethanol
Yield: 46.3%
C: calc.: 48.52, found: 48.7
H: calc.: 5.87, found: 5.6
Cl: calc.: 5.51, found: 5.6
N: calc.: 10.88, found: 10.7
O: calc.: 29.21, found: 29.4
UV: solvent: 0.1N HCl, 200 (4.29),210 (4.45),230 (4.53),286 (3.89),302 (s,3.59)

2-Methyl-4-chloro-5-((2-(4-(3-trifluoromethylphenyl) piperazinyl-1)ethyl)amino-3(2H)-pyridazinone Salt: 3.0 HCl; solvate: 2.25 H2O
M.p.: 120–126 deg. C., precipitn.: ethanol, diethyl ether
Yield: 38.4%
C: calc.: 38.33, found: 38.7
H: calc.: 5.05, found: 4.6
Cl: calc.: 25.15, found: 25.4
Cl—: calc.: 18.89, found: 19.1
N: calc.: 12.42, found: 12.4
O: calc.: 8.93, found: 9.3
F: calc.: 10.07, found: 9.6
UV: solvent: ethanol, 208 (4.44),232 (4.51),256 (4.20),294 (3.95),304 (s,3.91)

2-Methyl-5-chloro-4-((2-(4-(3,5-dichlorophenyl)-piperazinyl-1) ethyl)amino)-3(2H)-pyridazinone Salt: 0.75 HCl; solvate: 0.35 H2O
M.p.: 208–221 deg. C., precipitn.: ethanol, diethyl ether
Yield: 50.3%
C: calc.: 45.34, found: 45.2
H: calc.: 4.800, found: 4.7
Cl: calc.: 29.52, found: 30.0
Cl—: calc.: 5.90, found: 6.3

N: calc.: 15.55, found: 15.3
O: calc.: 4.80, found: 4.7

2-Methyl-4-chloro-5-((2-(4-(3-chlorophenyl)piperazinyl-1)ethyl) amino)-3(2H)-pyridazinone Salt: 1.25 HCl; solvate: 0.4 H2O
M.p.: 211–219 deg. C., purif. by chromatography
Yield: 32.9%
C: calc.: 46.93, found: 47.2
H: calc.: 5.23, found: 5.3
Cl: calc.: 26.48, found: 26.0
Cl−: calc.: 10.19, found: 10.1
N: calc.: 16.10, found: 16.3
O: calc.: 10.19, found: 10.1

2-Methyl-4-chloro-5-((2-(4-(2-fluorophenyl)piperazinyl-1) ethyl)amino)-3(2H)-pyridazinone Salt: 1.0 HBr; solvate: 0.65 H2O
M.p.: 240–243 deg. C., recryst.: ethanol
Yield: 42.4%
C: calc.: 44.54, found: 44.6
H: calc.: 5.12, found: 5.2
Cl: calc.: 7.73, found: 7.5
N: calc.: 15.28, found: 15.0
O: calc.: 5.76, found: 5.6
F: calc.: 4.14, found: 3.6
Br−: calc.: 17.43, found: 17.5
UV: solvent: 0.1N HCl, 212 (s,4.30),230 (4.56),288 (3.89),304 (s,3.78)

2-Methyl-4-chloro-5-((2-(4-(4-fluorophenyl)piperazinyl-1) ethyl)amino)-3(2H)-pyridazinone Salt: 2.0 HCl; solvate: 2.25 H2O
M.p.: 155–161 deg. C., recryst.: ethanol
Yield: 18.7%
C: calc.: 42.60, found: 42.9
H: calc.: 5.78, found: 5.3
Cl: calc.: 22.19, found: 22.4
Cl−: calc.: 14.79, found: 14.7
N: calc.: 14.61, found: 14.8
O: calc.: 10.85, found: 11.0
F: calc.: 3.96, found: 3.6
UV: solvent: ethanol, 204 (4.34),208 (4.34),232 (4.54),292 (3.93),304 (s,3.89)

2-Methyl-4-chloro-5-((2-(4-(4-nitrophenyl)piperazinyl-1) ethyl)amino)-3(2H)-pyridazinone Salt: 0.7 HCl; solvate: 0.1 H2O
M.p.: 242–251 deg. C; recryst.: ethanol
Yield: 10.7%
C: calc.: 48.60, found: 48.8
H: calc.: 5.25, found: 5.4
Cl: calc.: 14.34, found: 14.3
Cl−: calc.: 5.91, found: 5.5
N: calc.: 20.00, found: 19.8
O: calc.: 11.80, found: 11.7
UV: solvent: ethanol, 208 (4.28),232 (4.47),296 (3.81),312 (3.83),382 (4.13)

2-Methyl-4-chloro-5-((2-(4-(pyridyl-2)piperazinyl-1)ethyl) amino)-3(2H)-pyridazinone Salt: 2.0 HCl; solvate: 0.35 H2O
M.p.: 222–229 deg. C., recryst.: ethanol
Yield: 36.6%
C: calc.: 44.89, found: 45.1
H: calc.: 5.58, found: 5.5
Cl: calc.: 24.85, found: 24.8
Cl−: calc.: 16.56, found: 16.7
N: calc.: 19.63, found: 19.6
O: calc.: 5.05, found: 5.0

2-t-Butyl-4-chloro-5-((2-(4-(2-methoxyphenyl)piperazinyl-1) ethyl)amino)-3(2H)-pyridazinone Salt: 1.5 fumarate; solvate: 1.2 H2O
M.p.: 220–224 deg. C.,
Yield: 66.5%
C: calc.: 52.67, found: 52.5
H: calc.: 6.29, found: 6.3
Cl: calc.: 5.76, found: 5.9
N: calc.: 11.38, found: 11.4
O: calc.: 23.91, found: 23.9
UV: solvent: 0.1N HCl, 212 (4.68),230 (4.64),282 (4.02),312 (s,3.68)

2-(Dimethylaminoethyl)-4-chloro-5-((2-(4-(2-methoxyphenyl) piperazinyl-1)ethyl)amino)-3(2H)-pyridazinone Salt: 2.0 fumarate; solvate: 2.5 H2O
M.p.: 110–115 deg. C.,
Yield: 52.2%
C: calc.: 48.91, found: 49.1
H: calc.: 6.23, found: 5.9
Cl: calc.: 4.88, found: 5.0
N: calc.: 11.80, found: 11.8
O: calc.: 28.08, found: 28.2
UV: solvent: 0.1N HCl, 210 (4.49),232 (4.57),282 (3.95)309 (s,3.81)

2-Hydroxyethl-4-chloro-5-((2-(4-(2-methoxyphenyl)-piperazinyl-1-)ethyl)amino-3(2H)-pyridazinone Salt: 2.9 HCl; solvate: 2.7 H2O
M.p.: 130–141 deg. C., recryst.: acetone
Yield: 47.3%
C: calc.: 40.17, found: 40.6
H: calc.: 6.09, found: 5.8
Cl: calc.: 24.34, found: 24.4
Cl−: calc: 18.10, found 18.3
N: calc.: 12.33, found: 12.6
O: calc.: 16.05, found: 16.4
UV: solvent: ethanol, 212 (418),232 (4.54),286, (4.00),304 (s,3.85)

2-Hydroxyethyl-4chloro-5-((2-(4-(3-trifluoromethylphenyl) piperazinyl-1)ethyl)amino)-3-(2H)-pyridazinone Salt: 2.75 HCl; solvate: 2.0 H2O
M.p.: 117–121 deg. C. recryst.: ethanol
Yield: 29.1%
C: calc.: 39.20, found: 39.2
H: calc.: 5.15, found: 4.5
Cl: calc.: 22.84, found: 23.2
Cl−: calc.: 16.75, found: 16.6
N: calc.: 12.03, found: 12.0
O: calc.: 10.99, found: 11.3
F: calc.: 9.79; found: 9.8
UV: solvent: ethanol, 206 (4.41),234 (4.48),256 (4.19),294 (3.99),304 (s,3.95)

2-Phenyl-4-chloro-5-((2-(4-(2-methoxyphenyl)piperazinyl-1) ethyl)amino)-3(2H)-pyridazinone Salt: 1.0 HBr; solvate: 0.5 ethanol . 1.0 H2O
M.p.: 140–147 deg. C., recryst.: ethanol
Yield: 33.5%
C: calc.: 51.30, found: 51.7
H: calc.: 5.74, found: 5.8
Cl: calc.: 6.31, found: 6.2

N: calc.: 12.46, found: 12.2
O: calc.: 9.97, found: 10.1
Br—: calc.: 14.22, found: 14.0

2-Methyl-4-chloro-5-(methyl-(3-(4-(2-methoxyphenyl) piperazinyl-1)propyl)amino)-3(2H)-pyridazinone Salt: 1.0 fumarate; solvate: 0.5 H2O
M.p.: 169–173 deg. C; recryst.: ethanol
Yield: 6.1%
C: calc.: 54.28, found: 54.0
H: calc.: 6.26, found: 6.2
Cl: calc.: 6.68, found: 6.6
N: calc.: 13.19, found: 13.5
O: calc.: 19.58, found: 19.3

2-Methyl-4-chloro-5-((3-(4-(2-hydroxy-4-methylphenyl) piperazinyl-1)propyl)amino)-3(2H)-pyridazinone Salt: 1.0 fumarate ; solvate: 0.5 H2O
M.p.: 175–181 deg. C., recryst.: ethanol
Yield: 69.1%
C: calc.: 53.44, found: 52.7
H: calc.: 6.04, found: 6.3
Cl: calc.: 6.86, found: 6.9
N: calc.: 13.55, found: 13.7
O: calc.: 20.12, found: 20.4

2-Methyl-4-chloro-5-((3-(4-(2-ethoxy-4-methylphenyl) piperazinyl-1)propyl)yamino)-3(2H)-pyridazinone Salt: 2.4 HCl; solvate: 2.2 H2O
M.p.: 196–203 deg. C.,
Yield: 48.1%
C: calc.: 46.1, found: 45.8
H: calc.: 6.78, found: 6.5
Cl: calc.: 22.03, found: 22.5
Cl—: calc.: 15.55, found: 15.3
N: calc.: 12.80, found: 12.9
O: calc.: 12.28, found: 12.3

2-Methyl-4-chloro-5-((3-(4-(2-methylphenyl)piperazinyl-1) propyl)amino)-3(2H)-pyridazinone Salt: 1.0 fumarate; solvate: 0.5 H2O
M.p.: 176–184 deg. C.,
Yield: 40.%
C: calc.: 55.14, found: 54.7
H: calc.: 6.24, found: 6.2
Cl: calc.: 7.08, found: 7.3
N: calc.: 13.98, found: 14.1
O: calc.: 17.56, found: 17.7
UV: solvent: 0.1N HCl, 208 (4.47),232 (4.56),290 (3.88),302 (s,3.84)

2-Methyl-4-chloro-5-((3-(4-(2-fluorophenyl)piperazinyl-1) propyl)amino)-3(2H)-pyridazinone Salt: 1.0 fumarate; solvate: 1.0 H2O
M.p.: 176–179 deg. C., precipitn.: ethanol, acetone
Yield: 42.1%
C: calc.: 51.41, found: 51.2
H: calc.: 5.69, found: 5.4
Cl: calc.: 6.90, found: 7.1
N: calc.: 13.63, found: 13.7
O: calc.: 18.68, found: 18.8
F: calc.: 3.70, found: 3.8
UV: solvent: 0.1N HCl, 204 (4.39),232 (4.59),290 (3.89),305 (s,3.86)

2-Methyl-4-chloro-5-((3-(4-(4-fluorophenyl))piperazinyl-1) propyl)amino)-3(2H)-pyridazinone Salt: 3.0 HCl; solvate: 1.5 H2O
M.p.: 132–139 deg. C., recryst.: acetone
Yield: 34.7%
C: calc.: 41.88, found: 42.2
H: calc.: 5.47, found: 5.6
Cl: calc.: 27.47, found: 27.2
Cl—: calc.: 20.6, found: 20.8
N: calc.: 13.57, found: 13.7
O: calc.: 7.75, found: 7.9
F: calc.: 3.68, found: 3.4

2-Methyl-4-chloro-5-((3-(4-(pyridyl-2)piperazinyl-1)propyl) amino)-3(2H)-pyridazinone Salt: 2.0 HCl; solvate: 0.35 H2O
M.p.: 200–214 deg. C., recryst.: ethanol
Yield: 42.1%
C: calc.: 46.19, found: 45.9
H: calc.: 5.86, found: 5.7
Cl: calc.: 24.06, found: 24.4
Cl—: calc.: 16.04, found: 16.3
N: calc.: 19.01, found: 19.1
O: calc.: 4.89, found: 4.9

2-Methyl-4-chloro-5-((6-(4-(2-methoxyphenyl)piperazinyl-1) hexyl)amino)-3(2H)-pyridazinone Salt: 2.0 HCl; solvate: 1.5 H2O
M.p.: 160–175 deg. C; recryst.: ethanol
Yield: 38.0.%
C: calc.: 49.4, found: 50.3
H: calc.: 7.16, found: 6.8
Cl: calc.: 19.88, found: 19.4
Cl—: calc.: 13.25, found: 13.1
N: calc.: 13.09, found: 13.2
O: calc.: 10.47, found: 10.3
UV: solvent: ethanol, 212 (4.46),216 (s,4.45),234 (4.50),286 (3.96),304 (s,3.87)

EXAMPLE 8

2-Methyl-5-((2-(4-(2-methoxyphenyl)-1-piperazinyl)ethyl)amino)-3(2H)-pyridazinone 3.0 g (0.00794 mol) of 4-chloro-2-methyl-5-((2-(4-(2-methoxyphenyl)-1-piperazinyl)ethyl)amino)-3(2H)-pyridazinone are dissolved in 10 ml of absolute ethanol, 1.38 g (0.01 mol) of potassium carbonate and 0.3 g of Pd/C (10%) are added, and hydrogenation is carried out at room temperature until hydrogen uptake ceases. Removal of the catalyst and of inorganic material by filtration is followed by concentration in vacuo, resulting in 2.5 g of 2-methyl-5-((2-(4-(2-methoxyphenyl)-1-piperazinyl)ethyl)amino)-3(2H)-pyridazinone (91.7% of theory) as a colourless crystalline residue which is dissolved in hot isopropanol, and ethereal hydrochloric acid is added. 2.0 g (66.3% of theory) of hydrochloride of m.p. 237°–245° C. are produced; C 55.6%, H 7.0%, Cl(tot) 9.3%, Cl— 9.3%, N 18.3%, O 9.8%.

EXAMPLE 9

2-methyl-4-((2-(4-(2-methoxyphenyl)-1-piperazinyl)ethyl)amino)-3(2H)-pyridazinone 1.66 g (0.00312 mol) of 6-chloro-2-methyl-4-((2-(4-(2-methoxyphenyl)-1-piperazinyl)ethyl)amino)-1-3(2H)-pyridazinone in 100 ml of ethanol are hydrogenated with 0.0046 mole of NaOH and 100 mg of 10% palladium-charcoal at 60° C. for 1 hour until hydrogen uptake ceases; the catalyst is removed by filtration, the filtrate is concentrated and the residue is extracted with hot absolute ethanol, which is then acidified with alcoholic hydrochloric acid. 1.28 g of 2-methyl-4-((2-(4-(2- methoxyphenyl)-1-piperazinyl)ethyl)amino)-3(2H)-pyridazinone (81.5% of theory) are produced as colourless crystalline hydrochloride of m.p. 235°–244° C. (with decomposition); C 40.3%, H 6.4%, Cl— 24.3%, N 13.9%, O 15.0%.

The following are prepared in an analogous manner:

4((2-(4-(2-Hydroxyphenyl)piperazinyl-1)ethyl)amino)-3(2H)-pyridazinone

Salt: 1.0 HBr;
M.p.: 253–260 deg. C., recryst.: ethanol
Yield: 73.3%
C: calc.: 48.49, found: 48.5
H: calc.: 5.60, found: 5.8
N: calc.: 17.67, found: 17.5
O: calc.: 8.07, found: 8.4
Br: calc.: 20.16, found: 20.1

2-Methyl-4-((2-(4-phenylpiperazinyl-1)ethyl)amino)-3(2H) pyridazinone

Salt: 3.2 HCl; solvate: 2.6 H2O
M.p.: 225–230 deg. C., recryst.: ethanol
Yield: 59.7%
C: calc.: 42.81, found: 43.1
H: calc.: 6.64, found: 5.7
Cl—: calc.: 23.79, found: 24.0
N: calc.: 14.68, found: 14.9
O: calc.: 12.08, found: 12.3
UV: solvent: ethanol, 206 (4.33),252 (4.08),298 (4.16),310 (s,3.97)

2-Methyl-4-((2-(4-(2-methoxyphenyl)piperazinyl-1)ethyl) amino)-3(2H)-pyridazinone Salt: 2.0 HCl;
M.p.: 130–139 deg. C., recryst.: ethanol
Yield: 66.%
C: calc.: 51.93, found: 51.7
H: calc.: 6.54, found: 6.6
Cl—: calc.: 17.03, found: 17.1
N: calc.: 16.82, found: 16.7
O: calc.: 7.69, found: 7.9
UV: solvent: 1N HCl, 200 (3.81),204 (3.88),220 (4.14),282 (s,4.05),296 (4.12)

2-Methyl-4-(ethyl-(2-(4-(2-methoxyphenyl)piperazinyl-1) ethyl)amino)-3(2H)-pyridazinone Salt: 1.0 fumarate; solvate: 0.33 H2O
M.p.: 140–144 deg. C., precipitn.: ethanol, diethyl ether
Yield: 46.3%
C: calc.: 58.41, found: 58.3
H: calc.: 6.86, found: 7.0
N: calc.: 14.19, found: 14.1
O: calc.: 20.53, found: 20.5

2-Methyl-4-((2-(4-(2-methoxy-5-methylphenyl)piperazinyl-1) ethyl)amino)-3(2H)-pyridazinone Salt: 2.0 HCl;
M.p.: 235 deg. C (subl.), recryst.: ethanol
Yield: 49.4%
C: calc.: 52.58, found: 52.2
H: calc.: 6.83, found: 7.2
Cl—: calc.: 16.34, found: 16.6
N: calc.: 16.14, found: 16.0
O: calc.: 8.11, found: 8.0
UV: solvent: 0.1N HCl, 214 (4.57),224 (s,4.55),282 (4.03)

2-Methyl-4-((2-(4-(2-methoxy-4-methylphenyl)piperazinyl-1) ethyl)amino)-3(2H)-pyridazinone Salt: 1.25 fumarate ; solvate: 2.0 H2O
M.p.: 161–164 deg. C., recryst.: acetone
Yield: 70.1%
C: calc.: 53.52, found: 53.7
H: calc.: 6.74, found: 6.5
N: calc.: 13.00, found: 13.0
O: calc.: 26.73, found: 26.8
UV: solvent: 0.1N HCl, 206 (4.35),210 (4.34),290 (4.15)

2-Methyl-4-((6-(4-(2-methoxyphenyl)piperazinyl-1)hexyl) amino)-3(2H)-pyridazinone Salt: 3.0 HCl;
M.p.: 225–228 deg. C., precipitn.: ethanol, diethyl ether
Yield: 32.3%
C: calc.: 47.75, found: 47.8
H: calc.: 6.23, found: 6.2
Cl—: calc.: 23.49, found: 23.1
N: calc.: 14.47, found: 15.5
O: calc.: 7.07, found: 7.4

2-Methyl-4-((2-(4-(2-ethoxyphenyl)piperazinyl-1)ethyl) amino)-3(2H)-pyridazinone Salt: 2.0 HCl
M.p.: 196–204 deg. C.,
Yield: 66.4%
C: calc.: 53.03, found: 52.5
H: calc.: 6.79, found: 6.9
Cl—: calc.: 16.48, found: 16.3
N: calc.: 16.27, found: 16.2
O: calc.: 7.45, found: 8.0
UV: solvent: 0.1N HCl, 208 (4.28),227 (s,4.02),288 (4.05)

2-Methyl-4-((2-(4-(2-hydroxyphenyl)piperazinyl-1)ethyl)amino)-3(2H)-pyridazinone Salt: 2.25 HBr; solvate: 3.2 H2O
M.p.: 188–196 deg. C.,
Yield: 32.3%
C: calc.: 35.88, found: 36.1
H: calc.: 5.61, found: 5.1
N: Calc.: 12.31, found: 12.3
O: calc.: 14.62, found: 14.6
Br—: calc.: 31.59, found: 31.9
UV: solvent: 1N HCl, 206 (4.46),225 (s,4.11),288 (4.15),304 (s,4.01)

2-Methyl-4-((2-(4-(2,6-dimethylphenyl)piperazinyl-1)ethyl) amino)-3(2H)-pyridazinone Salt: 2.0 HCl; solvate: 0.6 H2O
M.p.: 235–240 deg. C., recryst.: ethanol
Yield: 47.7%
C: calc.: 53.67, found: 53.7
H: calc.: 7.16, found: 7.3
Cl—: calc.: 16.69, found: 16.4
N: calc.: 16.47, found: 16.5
O: calc.: 6.02, found: 6.0

2-Methyl-4-((2-(4-(3-trifluoromethylphenyl)piperazinyl-1) ethyl)amino-3(2H)-pyridazinone Salt: 2.2 HCl; solvate: 3.4 H2O
M.p.: 124–133 deg. C., recryst.: ethanol
Yield: 59.8%
C: calc.: 41.35, found: 41.8

H: calc.: 5.97, found: 5.9
Cl—: calc.: 14.92, found: 15.5
N: calc.: 13.40, found: 13.4
O: alc.: 13.46, found: 14.0
F: calc.: 10.90, found: 10.4
UV: solvent: ethanol, 204 ( 4.4),258 (4.20),300 (4.20),312 (s,4.05)

2-Methyl-4-((2-(4-(2-fluorophenyl)piperazinyl-1)ethyl)amino) -3(2H)-pyridazinone Salt: 1.2 HCl;
M.p.: 240–248 deg. C.,
Yield: 95.5%
C: calc.: 54.43, found: 54.4
H: calc.: 6.23, found: 6.4
Cl—: calc.: 11.34, found: 11.0
N: calc.: 18.67, found: 18.5
O: calc.: 4.27, found: 4.4
F: calc.: 5.06, found: 5.1

2-Methyl-4-((2-(4-(4-fluorophenyl)piperazinyl-1)ethyl)amino) 3(2H)-pyridazinone Salt: 2.6 HCl; solvate: 2.6 H2O
M.p.: 236–240 deg. C., recryst.: ethanol
Yield: 81.7%
C: calc.: 43.17, found: 43.6
H: calc.: 6.35, found: 5.7
Cl—: calc.: 19.49, found: 19.9
N: calc.: 14.81, found: 15.1
O: calc.: 12.18, found: 12.3
F: calc.: 4.02, found: 3.4
UV: solvent: ethanol, 206 (4.28),234 (4.03),244 (4.03),300 (4.18),312 (s,4.06)

2-t-Butyl-4-((2-(4-(2-methoxyphenyl)piperazinyl-1)ethyl) amino)-3(2H)-pyridazinone Salt: 2.0 HBr; solvate: 0.1 H2O
M.p.: 238–242 deg. C.,
Yield: 86.5%
C: calc.: 45.93, found: 46.1
H: calc.: 6.09, found: 6.2
N: calc.: 12.75, found: 12.5
O: calc.: 6.12, found: 6.4
Br—: calc.: 29.47, found: 28.8
UV: solvent: 0.1N HCl, 206 (4.51),225 (s,4.24),290 (4.20),312 (s,3.76)

2-t-Butyl-4-((2-(4-(3-trifluoromethyl)piperazinyl-1)ethyl) amino)-3(2H)-pyridazinone Salt: 2.0 HCl;
M.p.: 194–198 deg. C.; recryst.: ethanol
Yield: 48.8%
C: calc.: 50.81, found: 50.9
H: calc.: 6.09, found: 6.2
Cl—: calc.: 14.28, found: 14.1
N: calc.: 14.11, found: 14.2
O: calc.: 3.22, found: 3.2
F: calc.: 11.48, found: 11.4
UV: solvent: ethanol, 206 (3.79),260 (4.13),298 (4.10)

2-(2-Dimethylaminoethyl)-4-((2-(4-(2-methoxyphenyl)piperazinyl-1)ethyl)amino)-3(2H)-pyridazinone Salt: 3.0 HBr; solvate: 1.5 H2O
M.p.: 231–237 deg. C., precipitn.: ethanol, diethyl ether
Yield: 41.7% (crude mat.), 34.8% (purif.mat.)
C: calc.: 37.63, found: 37.8
H: calc.: 5.71, found: 5.6
N: calc.: 12.54, found: 12.4
O: calc.: 8.35, found: 8.4
Br—: calc.: 35.76, found: 35.8
UV: solvent: 0.1N HCl, 208 (4.43),229 (s,4.17),285 (s,4.26),296 (4.28),312 (s,4.12)

2-Hydroxyethyl-4-((2-(4-(2-methoxyphenyl)piperazinyl-1) ethyl)amino)-3(2H)-pyridazinone Salt: 3.15 HCl; solvate: 3.4 H2O
M.p.: 181–190 deg. C., recryst.: ethanol
Yield: 34.1%
C: calc.: 41.53, found: 41.6
H: calc.: 6.78, found: 6.5
Cl—: calc.: 20.32, found: 20.4
N: calc.: 12.74, found: 12.8
O: calc.: 18.63, found: 18.7
UV: solvent: ethanol, 210 (4.44),300 (4.15),312 (s,3.95)

2-(2-Hydroxyethyl)-4-((2-(4-(3-trifluoromethylphenyl) piperazinyl-1)ethyl)amino)-3(2H)-pyridazinone Salt: 2.4 HCl; solvate: 1.35 H2O
M.p.: 121–129 deg. C.; recryst.: acetone
Yield: 84.1%
C: calc.: 43.61, found: 44.0
H: calc.: 5.4, found: 5.3
Cl—: calc.: 16.26, found: 16.3
N: calc.: 13.38, found: 13.6
O: calc.: 10.24, found: 10.4
F: calc.: 10.90, found: 10.4
UV: solvent: ethanol, 206 (4.34),211 (s,4.27),260 (4.21),300 (4.21),312 (s,4.06)

2-Methyl-4-((2-(4-(pyridyl-2)piperazinyl-1)ethyl)amino)-3(2H)-pyridazinone

Salt: 2.4 HCl; solvate: 0.65 H2O
M.p.: 235–237 deg. C., recryst.: ethanol
Yield: 89.%
C: calc.: 46.67, found: 46.7
H: calc.: 6.29, found: 6.2
Cl—: calc.: 20.66, found: 20.6
N: calc.: 20.41, found: 20.1
O: calc.: 6.41, found: 6.4
UV: solvent: ethanol, 204 (4.10),252 (4.26),300 (4.26)

4-((3-(4-(2-Methoxyphenyl)piperazinyl-1)propyl)amino) -3(2H)-pyridazinone

Salt: 2.0 HCl; solvate: 0.1 H2O
M.p.: 245–256 deg. C.,
Yield: 81.9%
C: calc.: 51.61, found: 51.4
H: calc.: 6.55, found: 6.6
Cl—: calc.: 17.10, found: 17.1
N: calc.: 16.72, found: 16.7
O: calc.: 8.02, found: 8.0

4-((3-(4-(2-Ethoxyphenyl)piperazinyl-1)propyl)amino)-3(2H)pyridazinone

Salt: 2.1 HCl;
M.p.: 258–269 deg. C.,
Yield: 20.3%
C: calc.: 50.99, found: 50.9
H: calc.: 6.89, found: 6.7
Cl—: calc.: 16.64, found: 17.0
N: calc.: 15.65, found: 15.7
O: calc.: 9.83, found: 9.9

2-Methyl-4-((3-(4-(2-methoxyphenyl)piperazinyl-1)propyl) amino-3(2H)-pyridazinone Salt: 2.85 HCl;
M.p.: 238–246 deg. C., recryst.: ethanol
Yield: 86.2%
C: calc.: 47.87, found: 47.5
H: calc.: 6.67, found: 6.8
Cl−: calc.: 21.20, found: 21.1
N: calc.: 14.69, found: 14.7
O: calc.: 9.57, found: 9.8

2-Methyl-4-((3-(4-(2-hydroxy-4-methylphenyl)piperazinyl-1) propyl)amino)-3(2H)-pyridazinone Salt: 1.0 fumarate;
M.p.: 176–180 deg. C., recryst.: ethanol
Yield: 21.9%
C: calc.: 57.25, found: 57.7
H: calc.: 6.48, found: 6.8
N: calc.: 14.51, found: 14.2
O: calc.: 21.55, found: 21.0

2-Methyl-4-((3-(4-(2-ethoxy-4-methylphenyl)piperazinyl-1) propyl)amino)-3(2H)-pyridazinone Salt: 2.8 HCl; solvate: 1.75 H2O
M.p.: 202–205 deg. C.,
Yield: 97.3%
C: calc.: 48.59, found: 48.5
H: calc.: 7.24, found: 7.1
Cl−: calc.: 19.12, found: 19.4
N: calc.: 13.49, found: 13.5
UV: solvent: 0.1N HCl, 206 (4.35),296 (4.15),312 (s,3.92)

2-Methyl-4-((3-(4-(2-fluorophenyl)piperazinyl-1)propyl) amino)-3(2H)-pyridazinone Salt: 1.1 HCl;
M.p.: 232–238 deg. C.,
Yield: 97.2%
C: calc.: 56.08, found: 56.1
H: calc.: 6.56, found: 6.7
Cl−: calc.: 10.12, found: 10.2
N: calc.: 18.17, found: 18.1
O: calc.: 4.15, found: 4.2
F: calc.: 4.93, found: 4.7

2-Methyl-4-((3-(4-(4-fluorophenyl)piperazinyl-1)propyl)amino)-3(2H)-pyridazinone Salt: 2.0 HCl; solvate: 0.45 H2O
M.p.: 210–212 deg. C; recryst.: ethanol
Yield: 84.4%
C: calc.: 50.70, found: 50.9
H: calc.: 6.36, found: 6.4
Cl: calc.: 16.63, found: 16.9
Cl−: calc.: 16.63, found: 16.9
N: calc.: 16.42, found: 16.9
O: calc.: 5.44, found: 5.6
F: calc.: 4.46, found: 4.3

2-Methyl-4-((3-(4-(pyridyl-2)piperazinyl-1)propyl)amino)-3(2H)-pyridazinone

Salt: 2.0 HCl; solvate: 0.6 H2O
M.p.: 214–219 deg. C, recryst.: ethanol
Yield: 97.1%
C: calc.: 49.54, found: 50.1
H: calc.: 6.65, found: 7.0
Cl: calc.: 17.2, found: 16.6
Cl−: calc.: 17.2, found: 16.6
N: calc.: 20.39, found: 19.9
O: calc.: 6.21, found: 6.4

4-((4-(4-(2-Methoxyphenyl)piperazinyl-1)butyl)amino)-3(2H)-pyridazinone

Salt: 3.0 HCl; solvate: 0.38 H2O
M.p.: 170–182 deg. C.,
Yield: 79.6%
C: calc.: 48.21, found: 48.2
H: calc.: 6.54, found: 6.4
Cl: calc.: 22.39, found: 22.3
Cl−: calc.: 22.39, found: 22.3
N: calc.: 14.79, found: 14.7
O: calc.: 8.04, found: 8.0

2-Methyl-4-((4-(4-(2-methoxyphenyl)piperazinyl-1)butyl) amino)-3(2H)-pyridazinone Salt: 2.0 HCl; solvate: 0.25 H2O
M.p.: 193–202 deg. C., recryst.: ethanol
Yield: 76.7%
C: calc.: 53.51, found: 53.2
H: calc.: 7.07, found: 7.3
Cl−: calc.: 15.80, found: 15.8
N: calc.: 15.60, found: 15.3
O: calc.: 8.02, found: 7.8

5-((2-(4-(3-Trifluorophenyl)piperazinyl-1)ethyl)amino)-3(2H)-pyridazinone

Salt: 3.0 HCl; solvate: 0.3 H2O
M.p.: 197–205 deg. C; recryst. acetone
Yield: 66.9%
C: calc.: 42.35, found: 42.7
H: calc.: 4.93, found: 4.9
Cl: calc.: 22.06, found: 21.5
Cl−: calc.: 22.06, found: 21.5
N: calc.: 14.53, found: 14.8
O: calc.: 4.31, found: 4.5
F: calc.: 11.82, found: 11.6

2-Methyl-5-((2-(4-phenylpiperazinyl-1)ethyl)amino)-3(2H)-pyridazinone

Salt: 3.25 HCl; solvate: 1.15 H2O
M.p.: 251–256 deg. C, recryst.: ethanol
Yield: 76.2%
C: calc.: 45.11, found: 44.9
H: calc.: 6.36, found: 5.8
Cl: calc.: 25.46, found: 25.9
Cl−: calc.: 25.46, found: 25.9
N: calc.: 15.47, found: 15.7
O: calc.: 7.60, found: 7.7
UV: solvent: ethanol, 204 (s,4.59),208 (4.62),230 (4.66),252 (s,4.23), 284 (4.23)

2-Methyl-5-((2-(4-(2-methoxyphenyl)piperazinyl-1)ethyl) amino)-3(2H)-pyridazinone Salt: 1.0 HCl; solvate: 0.4 H2O
M.p.: 237–245 deg. C.,
Yield: 91.7%
C: calc.: 55.85, found: 55.6
H: calc.: 6.98, found: 7.0
Cl: calc.: 9.16, found: 9.3
Cl−: calc.: 9.16, found: 9.3
N: calc.: 18.09, found: 18.3
O: calc.: 9.92, found: 9.8

2-Methyl-5-((2-(4-(2-methoxy-4-methylphenyl)piperazinyl-1) ethyl)amino)-3(2H)-pyridazinone Salt: 1.5 fumarate ; solvate: 0.5 H2O M.p.: 176–178 deg. C., recryst.: acetone
Yield: 84.1%
C: calc.: 55.55, found: 55.6
H: calc.: 6.34, found: 6.5
N: calc.: 12.96, found: 12.8
O: calc.: 25.16, found: 25.1
UV: solvent: 0.1N HCl, 198 (4.34),212 (4.53),224 (4.53),280 (4.01)

2-Methyl-5-((2-(4-(2-methoxy-5-methylphenyl)piperazinyl-1) ethyl)amino)-3(2H)-pyridazinone Salt: 1.0 fumarate;
M.p.: 183–185 deg. C., recryst.: acetone
Yield: 76.8%
C: calc.: 58.34, found: 58.0
H: calc.: 6.60, found: 6.8
N: calc.: 14.79, found: 14.7
O: calc.: 20.27, found: 20.5
UV: solvent: 0.1N HCl, 210 ( 4.5),288 (4.02),304 (s,3.83)

2-Methyl-5-(ethyl-(2-(4-(2-methoxyphenyl)piperazinyl-1) ethyl)amino)-3(2H)-pyridazinone Salt: 3.0 HCl; solvate: 3.0 H2O
M.p.: 125–130 deg. C., precipitn.: isopropanol, diethyl ether
Yield: 62.3%
C: calc.: 44.91, found: 44.8
H: calc.: 7.16, found: 6.8
Cl: calc.: 19.88, found: 19.6
Cl−: calc.: 19.88, found: 19.7
N: calc.: 13.09, found: 13.1
O: Calc.: 14.96, found: 15.7

2-Methyl-5-((2-(4-(2-ethoxyphenyl)piperazinyl-1)ethyl) amino)-3(2H)-pyridazinone Salt: 1.0 fumarate; solvate: 0.6 H2O
M.p.: 175–178 deg. C.,
Yield: 64.8%
C: calc.: 57.04, found: 56.8
H: calc.: 6.70, found: 6.7
N: calc.: 14.46, found: 14.5
O: calc.: 21.80, found: 22.0
UV: solvent: 1N HCl, 208 (4.51),224 (4.51),276 (4.02)

2-Methyl-5-((2-(4-(2-hydroxyphenyl)piperazinyl-1)ethyl) amino)-3(2H)-pyridazinone Salt: 3.15 HBr; solvate: 1.3 H2O
M.p.: 190–198 deg. C., recryst.: ethanol
Yield: 44.2%
C: calc.: 33.60, found: 33.7
H: calc.: 4.77, found: 4.8
N: calc.: 11.52, found: 11.5
O: calc.: 8.69, found: 8.7
Br−: calc.: 41.42, found: 41.3
UV: solvent: 1N HCl, 210 (4.63),224 (4.53),280 (4.03)

2-Methyl-4-((2-(4-(2-methylphenyl)piperazinyl-1)ethyl) amino)-3(2H)-pyridazinone Salt: 1.5 fumarate;
M.p.: 178–182 deg. C., recryst.: ethanol
Yield: 93.%
C: calc.: 57.48, found: 57.8
H: calc.: 6.23, found: 6.2
N: calc.: 13.96, found: 13.9
O: calc.: 22.33, found: 22.4

2-Methyl-5-((2-(4-(2,6-dimethylphenyl)piperazinyl-1)ethyl) amino)-3(2H)-pyridazinone Salt: 2.0 HCl; solvate: 2.1 H2O
M.p.: 260 deg. C (subl.); recryst.: ethanol
Yield: 73.7%
C: calc.: 50.46, found: 51.0
H: calc.: 7.40, found: 7.4
Cl−: calc.: 15.68, found: 15.2
N: calc.: 15.49, found: 15.1
O: calc.: 10.97, found: 11.3
UV: solvent: ethanol, 206 (4.26),214 (4.35),224 (4.38),232 (4.38),280 (3.88)

2-Methyl-4-((2-(4-(2-fluorophenyl)piperazinyl-1)ethyl) amino)-3(2H)-pyridazinone Salt: 1.5 fumarate;
M.p.: 167–169 deg. C., recryst.: ethanol
Yield: 92.%
C: calc.: 54.65, found: 54.5
H: calc.: 5.58, found: 5.8
N: calc.: 13.85, found: 13.9
O: calc.: 22.16, found: 22.4
F: calc.: 3.76, found: 3.3

2-Methyl-5-((2-(4-(4-fluorophenyl)piperazinyl-1)ethyl)amino)-3(2H)-pyridazinone

Salt: 3.0 HCl; solvate: 0.7 H2O
M.p.: 162–168 deg. C ; recryst.: ethanol
Yield: 73.5%
C: calc.: 45.05, found: 45.5
H: calc.: 5.87, found: 5.7
Cl−: calc.: 23.46, found: 22.9
N: calc.: 15.45, found: 15.6
O: calc.: 6.00, found: 6.3
F: calc.: 4.19, found: 4.0
UV: solvent: ethanol, 208 (4.40),218 (4.39),230 (4.50),286 (3.94)

2-Methyl-5-((2-(4-(pyridyl-2)piperazinyl-1)ethyl)amino)-3(2H)-pyridazinone

Salt: 3.0 HCl; solvate: 0.5 H2O
M.p.: 260 deg. C (subl.); recryst.: ethanol
Yield: 80.9%
C: calc.: 44.40, found: 44.4
H: calc.: 6.06, found: 6.1
Cl: calc.: 24.58, found: 24.4
N: calc.: 19.42, found: 19.5
O: calc.: 5.55, found: 5.6

2-t-Butyl-5-((2-(4-(2-methoxyphenyl)piperazinyl-1)ethyl) amino)-3(2H)-pyridazinone Salt: 1 5 fumarate;
M.p.: 173–177 deg. C.,
Yield: 79.2%
C: calc.: 57.95, found: 57.6
H: calc.: 6.66, found: 6.7
N: calc.: 12.51, found: 12.4
O: calc.: 22.87, found: 23.3
UV: solvent: 0.1N HCl, 210 (4.48),226 (4.50),276 (4.05)

2-t-Butyl-5-((2-(4-(3-trifluoromethyl)piperazinyl-1)ethyl) amino)-3(2H)-pyridazinone Salt: 3.0 HCl; solvate: 0.25 H2O
M.p.: 228–230 deg. C; recryst.: acetone
Yield: 77.2%
C: calc.: 46.94, found: 47.0

H: calc.: 5.91, found: 5.9
Cl—: calc.: 19.79, found: 19.7
N: calc.: 13.03, found: 13.2
O: calc.: 3.72, found: 3.8
F: calc.: 10.61, found: 10.4
UV: solvent: ethanol, 210 (s,4.43),222 (s,4.50),230 (4.53),258 (4.23),278 (s,4.05)

2-(2-Dimethylaminoethyl)-5-((2-(4-(2-methoxyphenyl)piperazinyl-1)ethyl)amino)-3(2H)-pyridazinone Salt: 2.1 HBr; solvate: 0.1 H2O
M.p.: 236–246 deg. C., recryst.: isopropanol
Yield: 42.4%
C: calc.: 44.08, found: 44.1
H: calc.: 6.04, found: 6.4
N: calc.: 14.69, found: 14.5
O: calc.: 5.87, found: 5.9
Br—: calc.: 29.32, found: 29.1

2-Hydroxyethyl-5-((2-(4-(2-methoxyphenyl)piperazinyl-1) ethyl)amino)-3(2H)-pyridazinone Salt: 3.0 HCl; solvate: 0.6 H2O
M.p.: 190–200 deg. C., recryst.: ethanol
Yield: 70.2%
C: calc.: 46.23, found: 46.4
H: calc.: 6.37, found: 6.2
Cl: calc.: 21.55, found: 21.2
N: calc.: 14.19, found: 14.0
O: calc.: 11.67, found: 11.5

2-(2-Hydroxyethyl)-5-((2-(4-(3-trifluoromethyl)-piperazinyl-1) ethyl)amino)-3(2H)-pyridazinone Salt: 2.15 HCl; solvate: 1.05 H2O
M.p.: 190–194 deg. C ; recryst.: acetone
Yield: 88.2%
C: calc.: 44.86, found: 44.9
H: calc.: 5.60. found: 5.3
Cl—: calc.: 14.98, found: 15.3
N: calc.: 13.77, found: 14.0
O: calc.: 9.59, found: 9.8
F: calc.: 11.20, found: 10.7
UV: solvent: ethanol, 212 (4.33),218 (4.31),232 (4.35),258 (4.14),294 (3.91)

2-Phenyl-5-((2-(4-(2-methoxyphenyl)piperazinyl-1)ethyl) amino)-3(2H)-pyridazinone Salt: 1.0 HBr; solvate: 0.1 H2O
M.p.: 272–276 deg. C.,
Yield: 85.4%
C: calc.: 56.58, found: 56.8
H: calc.: 5.82, found: 5.9
N: calc.: 14.34, found: 14.3
O: calc.: 6.88, fOund: 7.3
Br—: calc.: 16.37, found: 16.4

2-Methyl-5-((3-(4-(2-methoxyphenyl)piperazinyl-1)propyl) amino-3(2H)-pyridazinone Salt: 3.0 HCl; solvate: 1.45 H2O
M.p.: 241–248 deg. C., precipitn.: ethanol, acetone
Yield: 61.7%
C: calc.: 46.29, found: 46.1
H: calc.: 6.52, found: 6.8
Cl—: calc.: 21.58, found: 21.6
N: calc.: 14.21, found: 14.3
O: calc.: 11.20, found: 11.2
UV: solvent: ethanol, 212 (4.56),218 (s,4.51),230 (4.51),284 (4.01)

1-Methyl-5-((3-(4-(2-ethoxy-4-methylphenyl)piperazinyl-1) propyl)amino)-3(2H)-pyridazinone Salt: 3.25 HCl; solvate: 3.1 H2O
M.p.: 218–227 deg. C.,
Yield: 65.4%
C: calc.: 45.05, found: 44.9
H: calc.: 7.28, found: 7.1
Cl—: calc.: 20.58, found: 20.6
N: calc.: 12.51, found: 12.6
O: calc.: 14.57, found: 14.8
UV: solvent: 0.1N HCl, 212 (4.49),228 (4.46),280 (3.98)

2-Methyl-4-((3-(4-(2-methylphenyl)piperazinyl-1)propyl) amino)-3(2H)-pyridazinone Salt: 1.0 fumarate;
M.p.: 194–197 deg. C., recryst.: ethanol
Yield: 94.6%
C: calc.: 60.38, found: 60.4
H: calc.: 6.83, found: 7.0
N: calc.: 15.31, found: 15.1
O: calc.: 17.49, found: 17.2

2-Methyl-5-((3-(4-(4-fluorophenyl)piperazinyl-1)propyl)amino)-3(2H)-pyridazinone Salt: 3.0 HCl; solvate: 0.9 H2O
M.p.: 176–181 deg. C; recryst.: ethanol
Yield: 76.8%
C: calc.: 45.90, found: 46.1
H: calc.: 5.97, found: 6.3
Cl—: calc.: 22.58, found: 22.4
N: calc.: 14.87, found: 15.1
O: calc.: 6.03, found: 6.6
F: calc.: 4.03, found: 3.5

2-Methyl-5-((3-(4-(pyridyl-2)piperazinyl-1)propyl)amino) 3(2H)-pyridazinone

Salt: 3.0 HCl;
M.p.: 232–239 deg. C; recryst.: ethanol
Yield: 70.6%
C: calc.: 46.64, found: 46.8
H: calc.: 6.22, found: 6.3
Cl: calc.: 24.29, found: 23.9
Cl—: calc.: 24.29, found: 23.9
N: calc.: 19.20, found: 19.4
O: calc.: 3.65, found: 3.6

2-Methyl-5-((4-(4-(2-methoxyphenyl)piperazinyl-1)butyl) amino)-3(2H)-pyridazinone Salt: 3.0 HCl; solvate: 1.0 H2O
M.p.: 168–176 deg. C., recryst.: ethanol
Yield: 66.8%
C: calc.: 48.15, found: 47.6
H: calc.: 6.87, found: 6.8
Cl—: calc.: 21.32, found: 21.3
N: calc.: 14.04, found: 14.0
O: calc.: 9.62, found: 9.4

2-Methyl-5-((6-(4-(2-methoxyphenyl)piperazinyl-1)hexyl) amino)-3(2H)-pyridazinone Salt: 3.0 HCl; solvate: 0.15 H2O
M.p.: 174–185 deg. C., precipitn.: ethanol, diethyl ether
Yield: 79.2%
C: calc.: 51.65, found: 51.7
H: calc.: 7.15, found: 7.2
Cl—: calc.: 20.79, found: 20.4

N: calc.: 13.69, found: 13.6
O: calc.: 6.72, found: 6.7

EXAMPLE 10

5-Methoxy-2-methyl-4-((2-(4-(2-methoxyphenyl)-1-piperazinyl)ethyl)amino)-3(2H)-pyridazinone 4.2 g (0.011 mol) of 5-chloro-2-methyl-4-((2-(4-(2-methoxyphenyl)-1-piperazinyl)ethyl)amino)-3(2H)-pyridazinone are heated in methanol, in which 0.010 mol of sodium methylate is dissolved, under reflux for 50 hours and then concentrated in vacuo. The residue is taken up in water, when 1.6 g of 5-methoxy-2-methyl-4-((2-(4-(2-methoxyphenyl)-1-piperazinyl)ethyl)amino)-3(2H)-pyridazinone (38.9% of theory) precipitate out. The solid is filtered off with suction, dried, dissolved in acetone and converted by addition of fumaric acid at the reflux temperature into 1.50 g (24.5% of theory) of fumarate, m.p. 144°–148° C.; C 54.0%, H 6.1%, N 12.5%, O 27.4%, UV in 0.1N H
Cl: 208(4.42), 226(S,4.22), 300(4.47).

EXAMPLE 11

5-Chloro-4-((2-(4-(3-trifluoromethylphenyl)-1-piperazinyl)ethyl)amino)-3(2H)-pyridazinone 4.25 g (0.0093 mol) of 2-t-butyl-5-chloro-4-((2(4-(3-trifluoromethylphenyl)-1-piperazinyl)ethyl)amino)-3(2H)-pyridazinone are stirred with 50 ml of concentrated aqueous hydrochloric acid at room temperature for 72 hours, made basic and extracted 3 times with chloroform, 10 the organic phase is concentrated and dried with sodium sulphate, and the residue is triturated with acetone. The crystalline precipitate of 5-chloro-4-((2-(4-(3-trifluoromethylphenyl)-1-piperazinyl)ethyl-)amino)-3(2H)-pyridazinone weighs 2.40 g (47.7% of theory). It is converted by dissolving in 100 ml of hot absolute ethanol and adding ethereal hydrochloric acid into 2.20 g (46.7% of theory) of dihydrochloride of m.p. 220°–223° C.; C 40.6%, H 4.2%, Cl(tot) 21.1%, Cl— 14.2%, F 11.5%, N 13.9%, O 8.7%, UV in 0.1N HCl: 208(4.42), 226(S,4.22), 300(4.47).

The following substance is prepared in an analogous manner:

4-Chloro-5-((2-(4-(2-methoxyphenyl)-1-piperazinyl)ethyl)amino)-3(2H)-pyridazinone salt: 1.5 fumarate; solvate: 2.0 $H_2O$
m.p.: 211°–213° C., recryst.: ethanol
yield: 58.5% of theory.
C: calc.: 48.13, found: 48.3
H: calc.: 5.62, found: 5.4
Cl: calc.: 6.18, found: 5.6
N: calc.: 12.20, found: 12.4
O: calc.: 27.87, found: 28.3
UV: solvent: 0.1N HCl, 210 (4.38), 228 (4.42), 280 (3.81), 304 (3.72)

EXAMPLE 12

2-Methyl-6-chloro-4-((3-(4-(2-methoxyphenyl)-1-piperazinyl)propyl)amino)-3(2H)-pyridazinone 6.0 g (0.0159 mol) of finely ground 6-chloro-4((3-(4-(2-methoxyphenyl)-1-piperazinyl)propyl)amino)-3(2H)-pyridazinone are suspended in 100 ml of 2N NaOH and stirred with 1.51 ml of dimethyl sulphate (0.0159 mol) at 60° C. for 2 hours and then cooled; the mixture is extracted several times which chloroform, and the organic phase is dried and concentrated. 3.50 g (56.2% of theory) of impure 2-methyl-6-chloro-4-((3-(4-(2-methoxyphenyl)-1-piperazinyl)propyl)amino)-3(2H)-pyridazinone crystallize out of the oily residue overnight and are purified by preparative chromatography on silica gel (Waters PrepPak). The pure fraction is dissolved in isopropanol, and ethereal hydrochloric acid is added and gives 0.85 g (11.2% of theory) of white crystalline dihydrochloride, m.p. 218°–229° C.; C 40.6%, H 4.2%, Cl(tot) 21.1%, Cl— 14.2%, F 11.5%, N 13.9%, O 8.7%.

EXAMPLE 13

6-Chloro-2-ethyl-4-((3-(4-(2-methoxyphenyl)-1-piperazinyl)propyl)amino)-3(2H)-pyridazinone 1.80 g (0.00474 mol) of finely ground 6-chloro-4-((3-(4-(2-methoxyphenyl)-1-piperazinyl)propyl)amino)-3(2H)-pyridazinone are suspended in 80 ml of 2N NaOH, 1.8 ml (0.014 mol) of ethyl iodide are added, and the mixture is stirred at room temperature for 90 minutes; then 1.8 ml of ethyl iodide are again added and the mixture is stirred for a further 2 hours. The solvent is evaporated off, the residue is taken up in water and extracted with chloroform. The organic phase is dried and concentrated, leaving a brown oil which, on dissolution in ethanol and addition of ethanolic hydrochloric acid, provides 0.70 g (30.6% of theory) of pure dihydrochloride of 6-chloro-2-ethyl-4-((3-(4-(2-methoxyphenyl)-1-piperazinyl)propyl)amino)-3(2H)-pyridazinone, m.p. 202°–207° C., as white crystalline substance; C 49.4%, H 6.4% Cl(tot) 21.8%, Cl— 14.6%, N 14.3%, O 7.7%.

EXAMPLE 14

6-Chloro-4-((4-(4-(2-methoxyphenyl)-1-piperazinyl)butyl)amino)-3(2H)-pyridazinone 4.00 g (0.00985 mol) of 6-chloro-3-methoxy-4-((4-(4-(2-methoxyphenyl)-1-piperazinyl)butyl)amino)-pyridazine are dissolved in 40 ml of glacial acetic acid, and 40 ml of 63% strength HBr are added. The mixture is refluxed for 2 hours, 200 ml of water are added, 30% strength KOH is added to pH 6, and the precipitated substance is filtered off with suction and thoroughly washed with water. 3.85 g (99.7% of theory) of 6-chloro-4-((4-(4-(2-methoxyphenyl)-1-piperazinyl)butyl-)amino)-3(2H)-pyridazinone are obtained, purified by recrystallization from ethanol with addition of charcoal, and immediately added to a solution of ethanolic hydrochloric acid, resulting in 3.26 g (68.7% of theory) of pure dihydrochloride, m.p. 247°–252° C.; C 47.2%, H 6.0%, Cl(tot) 21.9%, Cl— 14.6%, N 14.4%, O 10.0%.

The starting compounds required for carrying out the stated example are prepared as stated hereinafter:

6-Chloro-3-methoxy-4-((4-(4-(2-methoxyphenyl)-1-piperazinyl)butyl)amino)pyridazine 3.28 g (0.008 mol) of 3,6-dichloro-4-((4-(4-(2-methoxyphenyl)-1-piperazinyl)butyl)amino)pyridazine and 0.32 g (0.008 mol) of sodium methylate in 150 ml of methanol are stirred at 50° for 144 h. The mixture is subsequently concentrated in vacuo, the residue is dissolved in chloroform and extracted by shaking with water. The solvent is removed by evaporation, the residue is dissolved in ether, the solution is filtered to clarify and the hydrochloride of 6-chloro-3-methoxy-4-((4-(4-(2-methoxyphenyl)-1-piperazinyl)butyl)amino)-pyridazine (3.14 eq. of HCl) of m.p.: 139°–150° C. is precipitated with ethereal HCl, yield: 91.1% of theory.

3,6-Dichloro-4-((4-(4-(2-methoxyphenyl)-1-piperazinyl)butyl)amino)pyridazine 9.25 g (0.050 mol) of 3,4,6-trichloropyridazine are stirred with 6.90 g (0.050 mol) of powdered anhydrous potassium carbonate and 13.15 g (0.050 mol) of 1-(4-aminobutyl)-4-(2-methoxyphenyl)piperazine in 1350 ml of dry acetonitrile at room temperature for 96 hours. The mixture is subsequently filtered with suction, and the filtrate is concentrated in vacuo. The residue is taken up in ethanol, and the trihydrochloride of 3,6-dichloro-4-((4-(4-(2-methoxyphenyl)-1-piperazinyl)-butyl)amino)pyridazine of m.p.: 155°–170° C. is precipitated with ethereal HCl; yield: 54.2% of theory.

The following compounds are prepared in an analogous manner:

6-Chloro-4-((2-(4-(2-methoxyphenyl)piperazinyl-1)ethyl)amino)-3(2H)-pyridazinone Salt: 2.1 HCl; solvate: 1.16 H2O
M.p.: 241–247 deg. C;
Yield: 86.8%
C: calc.: 44.26, found: 44.6
H: calc.: 5.77, found: 5.3
Cl: calc.: 23.82, found: 23.7
Cl—: calc.: 16.14, found: 16.1
N: calc.: 15.18, found: 15.1
O: calc.: 10.96, found: 10.9

2-Methyl-6-chloro-4-((2-(4-(2-methoxyphenyl)piperazinyl-1)ethyl) amino)-3(2H)-pyridazinone Salt: 2.0 HCl ; solvate: 0.05 H2O
M.p.: 232–237 deg. C
Yield: 63.0%
C: calc.: 47.79, found: 47.8
H: calc.: 5.82, found: 5.8
Cl: calc.: 23.67, found: 23.5
Cl—: calc.: 15.83, found: 15.8
N: calc.: 15.48, found: 15.4
O: calc.: 7.24, found: 7.2

6-Chloro-4-((2-(4-(2-iso-propoxyphenyl)piperazinyl-1)ethyl) amino)-3(2H)-pyridazinone Salt: 1.0 HBr; solvate: 0.3 H2O
M.p. 280–295 deg. C., recryst.: ethanol
Yield: 12.7%
C: calc.: 47.72, found: 48.1
H: calc.: 5.82, found: 6.0
Cl: calc.: 7.41, found: 6.6
N: calc.: 14.64, found: 14.6
O: calc.: 7.70, found: 8.0
Br—: calc.: 16.71, found: 16.7
UV: solvent: 1N HCl, 210 (4.48),234 (s,4.08), 246 (s,3.94),288 (4.13),309 (s,3.82)

6-Chloro-4-((3-(4-(2-methoxyphenyl)piperazinyl-1)propyl) amino)-3(2H)-pyridazinone Salt: 2.0 HCl; solvate: 0.35 H2O
M.p.: 267–275 deg. C;
Yield: 88.1%
C: calc.: 47.3, found: 47.2
H: calc.: 5.89, found: 5.8
Cl: calc.: 23.27, found: 23.1
Cl—: calc.: 15.51, found: 15.5
N: calc.: 15.32, found: 15.3
O: calc.: 8.23, found: 8.2

6-Chloro-4-((3-(4-(2-methoxy-4-methylphenyl)piperazinyl-1) propyl)amino)-3(2H)-pyridazinone Salt: 2.0 HBr; solvate: 3.5 H2O
M.p.: 191–195 deg. C., recryst.: ethanol
Yield: 81.3%
C: calc.: 37.08, found: 37.3
H: calc.: 5.72, found: 5.2
Cl: calc.: 5.75, found: 5.5
N: calc.: 11.35, found: 11.4
O: calc.: 14.27, found: 14.7
Br—: calc.: 25.91, found: 25.9
UV: solvent: 0.1N HCl, 206 ( 4.6), 226 (s,4.19), 288 (4.28),309 (s,4.03)

2-Methyl-6-chloro-(3-(4-(2-ethoxyphenyl)piperazinyl-1) propyl)amino)-3(2H)-pyridazinone Salt: 2.0 HCl
M.p.: 211–215 deg. C;
Yield: 7.9%
C: calc.: 50.17, found: 50.3
H: calc.: 6.32, found: 6.4
Cl: calc.: 22.21, found: 21.9
Cl—: calc.: 14.81, found: 14.6
N: calc.: 14.63, found: 14.5
O: calc.: 6.68, found: 7.1

6-Chloro-2-methyl-4-((3-(4-(2-methoxyphenyl)piperazinyl-1) propyl)amino)-3(2H)-pyridazinone Salt: 2.0 HCl
M.p.: 218–229 deg. C.
Yield: 14.5%
C: calc.: 47.62, found: 47.1
H: calc.: 6.23, found: 6.0
Cl: calc.: 22.19, found: 22.7
Cl—: calc.: 14.80, found: 15.0
N: calc.: 14.61, found: 14.7
O: calc.: 9.35, found: 9.5

6-Chloro-2-ethyl-4-((3-(4-(2-methoxyphenyl)piperazinyl-1) propyl)amino)-3(2H)-pyridazinone Salt: 2.0 HCl; solvate: 0.35 H2O
M.p.: 202–207 deg. C
Yield: 30.6%
C: calc.: 49.51, found: 49.4
H: calc.: 6.38, found: 6.4
Cl: calc.: 21.92, found: 21.8
Cl—: calc.: 14.62, found: 14.6
N: calc.: 14.44, found: 14.3
O: calc.: 7.75, found: 7.7

6-Chloro-2-hydroxyethyl-4-((3-(4-(2-methoxyphenyl) piperazinyl-1)propyl)amino)-3(2H)-pyridazinone Salt: 2.0 HCl; solvate: 1.0 H2O
M.p.: 168–175 deg. C.
Yield: 25.8%
C: calc.: 46.84, found: 47.5
H: calc.: 6.29, found: 5.8
Cl: calc.: 20.74, found: 20.5
Cl—: calc.: 13.83, found: 13.9
N: calc.: 13.66, found: 13.5

EXAMPLE A

Determination of the affinity of compounds of the formula I for alpha$_1$ adrenoceptors.

The affinity of compounds of the general formula I for alpha$_1$ adrenoceptors was established using the method described by R. S. Williams, D. F. Dukes and R. F. Lefkowitz in J. Cardiovasc. Pharmacol. 3, 522–531 (1981). In this method the competitive displacement of tritiated prazosin (2-(4-(2-furoyl)-1-piperazinyl)-4-amino-6,7-dimethoxy-quinazoline) on rat-cardiac membranes by the test substances is measured, and the $IC_{50}$ (50% inhibition concentration) is determined as that concentration which brings about a 50% inhibition of the specific binding of tritiated prazosin to the $alpha_1$ adrenoceptors in rat cardiac membranes.

The concentration-independent inhibitor constants $K_1$-$alpha_1$ were determined from the $IC_{50}$ values as stated by Y. Cheng and H. W. Prusoff in Biochem. Pharmacol. 22, 3099–3108 (1973).

The results of these investigations are compiled in the table which follows:

Inhibition constants at alpha-1-adrenoceptor:

2-Methyl-5-bromo-4-((2-(4-(2-methoxyphenyl)piperazin-1) ethyl)amino)-3(2H)-pyridazinone
$Ki = 1.33$ 2-Methyl-4-bromo-5-((2-(4-(2-methoxyphenyl)piperazinyl-1) ethyl)amino)-3(2H)-pyridazinone
$Ki = 5.88$ 2-Methyl-5-chloro-4-((2-(4-(2-methoxyphenyl)piperazinyl-1) ethyl)amino)-3(2H)-pyridazinone
$Ki = 1.5$ 2-Methyl-4-chloro-5-((2-(4-(2-methoxyphenyl)piperazinyl-1) ethyl)amino)-3(2H)-pyridazinone
$Ki = 7.57$ 2-Methyl-4-chloro-5-((3-(4-(2-methoxyphenyl)piperazinyl-1) propyl)amino)-3(2H)-pyridazinone
$Ki = 32.2$ 2-Methyl-5-chloro-4-((3-(4-(2-methoxyphenyl)piperazinyl-1) propyl)amino)-3(2H)-pyridazinone
$Ki = 3.48$ 2-Methyl-4-chloro-5-((4-(4-(2-methoxyphenyl)piperazinyl-1) butyl)amino)-3(2H)-pyridazinone
$Ki = 6.05$ 2-Methyl-5-chloro-4-((4-(4-(2-methoxyphenyl)piperazinyl-1) butyl)amino)-3(2H)-pyridazinone
$Ki = 2.15$ 5-Chloro-4-((2-(4-(2-methoxyphenyl)piperazinyl-1)ethyl) amino)-3(2H)-pyridazinone
$Ki = 2.95$ 2-Methyl-5-chloro-4-((2-(4-phenylpiperazinyl-1)ethyl)amino)-3(2H)-pyridazinone
$Ki = 86.7$ 2-Methyl-5-chloro-4-((2-(4-(2-methoxy-5-methylphenyl) piperazinyl-1)ethyl)amino)-3(2H)-pyridazinone
$Ki = 6.01$ 2-Methyl-5-chloro-4-((2-(4-(2-methoxy-4-methylphenyl) piperazinyl-1)ethyl)amino)-3(2H)-pyridazinone
$Ki = 22.4$ 2-Methyl-5-chloro-4-((2-(4-(2-benzyloxyphenyl)-piperazinyl-1) ethyl)amino)-3(2H)-pyridazinone
$Ki = 2.54$ 2-Methyl-5-chloro-4-((2-(4-(2-hydroxyphenyl)piperazinyl-1) ethyl)amino)-3(2H)-pyridazinone
$Ki = 2.55$ 2-Methyl-5-chloro-4-((2-(4-(2-methylphenyl)piperazinyl-1) ethyl)amino)-3(2H)-pyridazinone
$Ki = 1.21$ 2-Methyl-5-chloro-4-((2-(4-(3-trifluoromethylphenyl) piperazinyl-1)ethyl)amino-3(2H)-pyridazinone
$Ki = 47.3$ 2-Methyl-5-chloro-4-((2-(4-(2-fluorophenyl)piperazinyl-1) ethyl)amino)-3(2H)-pyridazinone
$Ki = 2.51$ 2-t-Butyl-5-chloro-4-((2-(4-(2-methoxyphenyl)piperazinyl-1) ethyl)amino)-3(2H)-pyridazinone
$Ki = 42.2$ 2-(2-Dimethylaminoethyl)-5-chloro-4-((2-(4-(2-methoxyphenyl) piperazinyl-1)ethyl)amino)-3(2H)-pyridazinone
$Ki = 15.8$ 2-Hydroxyethyl-5-chloro-4-((2-(4-(2-methoxyphenyl) piperazinyl-1)ethyl)amino)-3(2H)-pyridazinone
$Ki = 2.42$ 2-Methyl-5-chloro-4-(N-methyl-N-(3-(4-(2-methoxyphenyl) piperazinyl-1)propyl)amino)-3(2H)-pyridazinone
$Ki = 12.9$ 2-Methyl-5-chloro-4-((3-(4-(2-hydroxy-4-methylphenyl) piperazinyl-1)propyl)amino)-3(2H)-pyridazinone
$Ki = 5.34$ 2-Methyl-5-chloro-4-((3-(4-(2-ethoxy-4-methylphenyl) piperazinyl-1)propyl)amino)-3(2H)-pyridazinone
$Ki = 4.99$ 2-Methyl-5-chloro-4-((3-(4-(2-methylphenyl)piperazinyl-1) propyl)amino)-3(2H)-pyridazinone
$Ki = 4.45$ 2-Methyl-5-chloro-4-((3-(4-(2-fluorophenyl)piperazinyl-1) propyl)amino)-3(2H)-pyridazinone
$Ki = 4.89$ 4-Chloro-5-((2-(4-(2-methoxyphenyl)piperazinyl-1)ethyl)amino) -3(2H)-pyridazinone
$Ki = 5.43$ 2-Methyl-4-chloro-5-((2-(4-phenylpiperazinyl-1)ethyl)amino)-3(2H)-pyridazinone
$Ki = 4.05$ 2-Methyl-4-chloro-5-((2-(4-(2-methoxy-4-methylphenyl) piperazinyl-1)ethyl)amino)-3(2H)-pyridazinone
$Ki = 31.4$ 2-Methyl-4-chloro-5-((2-(4-(2-methoxy-5-methylphenyl) piperazinyl-1)ethyl)amino)-3(2H)-pyridazinone
$Ki = 6.98$ 2-Methyl-4-chloro-5-(N-ethyl-(2-(4-(2-methoxyphenyl) piperazinyl-1)ethyl)amino)-3(2H)-pyridazinone
$Ki = 37.1$ 2-Methyl-4-chloro-5-((2-(4-(2-ethoxyphenyl)piperazinyl-1) ethyl)amino)-3(2H)-pyridazinone
$Ki = 7.59$ 2-Methyl-4-chloro-5-((2-(4-(2-hydroxyphenyl)piperazinyl-1) ethyl)amino)-3(2H)-pyridazinone
$Ki = 15.4$ 2-Methyl-4-chloro-5-((4-(2-hydroxy-4-methylphenyl)-piperazinyl -1)ethyl)amino)-3(2H)-pyridazinone
$Ki = 20.8$ 2-Methyl-4-chloro-5-((2-(4-(2-benzyloxyphenyl)-piperazinyl-1) ethyl)amino)-3(2H)-pyridazinone
$Ki = 2.0$ 2-Methyl-4-chloro-5-((2-(4-(2-methylphenyl)piperazinyl-1) ethyl)amino)-3(2H)-pyridazinone
$Ki = 6.27$ 2-Methyl-4-chloro-5-((2-(4-(3-trifluoromethylphenyl) piperazinyl-1)ethyl)amino)-3(2H)-pyridazinone
$Ki = 94.2$ 2-Methyl-4-chloro-5-((2-(4-(2-fluorophenyl)piperazinyl-1) ethyl)amino)-3(2H)-pyridazinone
$Ki = 28.2$ 2-t-Butyl-4-chloro-5-((2-(4-(2-methoxyphenyl)piperazinyl-1) ethyl)amino)-3(2H)-pyridazinone
$Ki = 12.8$ 2-(Dimethylaminoethyl)-4-chloro-5-((2-(4-(2-methoxyphenyl) piperazinyl-1)ethyl)amino)-3(2H)-pyridazinone
Ki=17.3

2-Hydroxyethl-4-chloro-5-((2-(4-(2-methoxyphenyl)-piperazinyl-1-)ethyl)amino-3(2H)-pyridazinone
Ki=10.8

2-Phenyl-4-chloro-5-((2-(4-(2-methoxyphenyl)piperazinyl-1) ethyl)amino)-3(2H)-pyridazinone
Ki=4.48

2-Methyl-4-chloro-5-(N-methyl-N-((3-(4-(2-methoxyphenyl) piperazinyl-1)propyl)amino)-3(2H)-pyridazinone
Ki=3.55

2-Methyl-4-chloro-5-((3-(4-(2-hydroxy-4-methylphenyl) piperazinyl-1)propyl)amino)-3(2H)-pyridazinone
Ki=4.33

2-Methyl-4-chloro-5-((3-(4-(2-ethoxy-4-methylphenyl) piperazinyl-1)propyl)amino)-3(2H)-pyridazinone
Ki=3.78

2-Methyl-4-chloro-5-((3-(4-(2-methylphenyl)piperazinyl-1) propyl)amino)-3(2H)-pyridazinone
Ki=31.4

2-Methyl-4-chloro-5-((3-(4-(2-fluorophenyl)piperazinyl-1) propyl)amino)-3(2H)-pyridazinone
Ki=32.8

2-Methyl-5-((2-(4-(2-methoxyphenyl)piperazinyl-1)ethyl) amino)-3(2H)-pyridazinone
Ki=190.0

4-((2-(4-(2-Methoxyphenyl)piperazinyl-1)ethyl)amino)-3(2H)-pyridazinone
Ki=42.2

4-((2-(4-(2-Hydroxyphenyl)piperazinyl-1)ethyl)amino)-3(2H)-pyridazinone
Ki=84.0

2-Methyl-4-((2-(4-phenylpiperazinyl-1)ethyl)amino)-3(2H) pyridazinone
Ki=90.3

2-Methyl-4-((2-(4-(2-methoxyphenyl)piperazinyl-1)ethyl) amino)-3(2H)-pyridazinone
Ki=15.7

2-Methyl-4-(N-ethyl-(2-(4-(2-methoxyphenyl)piperazinyl-1) ethyl)amino)-3(2H)-pyridazinone
Ki=68.0

2-Methyl-4-((2-(4-(2-methoxy-5-methylphenyl)piperazinyl-1) ethyl)amino)-3(2H)-pyridazinone
Ki=73.6

2-Methyl-4-((2-(4-(2-methoxy-4-methylphenyl)piperazinyl-1) ethyl)amino)-3(2H)-pyridazinone
Ki=171.0

2-Methyl-4-((2-(4-(2-ethoxyphenyl)piperazinyl-1)ethyl) amino)-3(2H)-pyridazinone
Ki=13.6

2-Methyl-4-((2-(4-(2-hydroxyphenyl)piperazinyl-1)ethyl) amino)-3(2H)-pyridazinone
Ki=65.5

2-Methyl-4-((2-(4-(3-trifluoromethylphenyl)piperazinyl-1) ethyl)amino-3(2H)-pyridazinone
Ki=175.0

2-Methyl-4-((2-(4-(2-fluorophenyl)piperazinyl-1)ethyl)amino) -3(2H)-pyridazinone
Ki=21.4

2-t-Butyl-4-((2-(4-(2-methoxyphenyl)piperazinyl-1)ethyl) amino)-3(2H)-pyridazinone
Ki=60.8

2-(2-Dimethylaminoethyl)-4-((2-(4-(2-methoxyphenyl) piperazinyl-1)ethyl)amino)-3(2H)-pyridazinone
Ki=437.0

2-Hydroxyethyl-4-((2-(4-(2-methoxyphenyl)piperazinyl-1) ethyl)amino-3(2H)-pyridazinone
Ki=17.7

4-((3-(4-(2-methoxyphenyl)piperazinyl-1)propyl)amino) -3(2H)-pyridazinone
Ki=26.1

4-((3-(4-(2-Ethoxyphenyl)piperazinyl-1)propyl)amino)-3(2H)-pyridazinone
Ki=13.0

2-Methyl-4-((3-(4-(2-methoxyphenyl)piperazinyl-1)propyl) amino-3(2H)-pyridazinone
Ki=24.7

2-Methyl-4-((3-(4-(2-Hydroxy-4-methylphenyl)-piperazinyl-1) propyl)amino)-3(2H)-pyridazinone
Ki=20.9

2-Methyl-4-((3-(4-(2-ethoxy-4-methylphenyl)piperazinyl-1) propyl)amino)-3(2H)-pyridazinone
Ki=13.6

2-Methyl-4-((3-(4-(2-fluorophenyl)piperazinyl-1)propyl) amino)-3(2H)-pyridazinone
Ki=30.2

4-((4-(4-(2-methoxyphenyl)piperazinyl-1)butyl)amino) -3(2H)-pyridazinone
Ki=4.64

2-Methyl-4-((4-(4-(2-methoxyphenyl)piperazinyl-1)butyl) amino)-3(2H)-pyridazinone
Ki=11.8

2-Methyl-5-((2-(4-phenylpiperazinyl-1)ethyl)amino)-3(2H)-pyridazinone
Ki=157.0

2-Methyl-5-((2-(4-(2-methoxy-4-methylphenyl)piperazinyl-1) ethyl)amino)-3(2H)-pyridazinone
Ki=207.0

2-Methyl-5-((2-(4-(2-methoxy-5-methylphenyl)piperazinyl-1) ethyl)amino)-3(2H)-pyridazinone
Ki=82.6

2-Methyl-5-(N-ethyl-(2-(4-(2-methoxyphenyl)piperazinyl-1) ethyl)amino)-3(2H)-pyridazinone
Ki=20.6

2-Methyl-5-((2-(4-(2-ethoxyphenyl)piperazinyl-1)ethyl) amino)-3(2H)-pyridazinone
Ki=103.0

2-Methyl-5-((2-(4-(2-hydroxyphenyl)piperazinyl-1)ethyl) amino)-3(2H)-pyridazinone
Ki=65.8

2-Methyl-5-((2-(4-(2-methylphenyl)piperazinyl-1)ethyl) amino)-3(2H)-pyridazinone
Ki=48.4

2-Methyl-4-((2-(4-(2-fluorophenyl)piperazinyl-1)ethyl) amino)-3(2H)-pyridazinone
Ki=89.4

2-t-Butyl-5-((2-(4-(2-methoxyphenyl)piperazinyl-1)ethyl) amino)-3(2H)-pyridazinone
Ki=6.03

2-(2-Dimethylaminoethyl)-5-((2-(4-(2-methoxyphenyl) piperazinyl-1)ethyl)amino)-3(2H)-pyridazinone
Ki=229.0

2-Hydroxyethyl-5-((2-(4-(2-methoxyphenyl)piperazinyl-1) ethyl)amino-3(2H)-pyridazinone
Ki=128.0

2-Phenyl-5-((2-(4-(2-methoxyphenyl)piperazinyl-1)ethyl) amino)-3(2H)-pyridazinone
Ki=61.6

2-Methyl-4-((3-(4-(2-methoxyphenyl)piperazinyl-1)propyl) amino-3(2H)-pyridazinone
Ki=40.5

2-Methyl-5-((3-(4-(2-ethoxy-4-methylphenyl)piperazinyl-1) propyl)amino)-3(2H)-pyridazinone Ki=23.3
2-Methyl-4-((3-(4-(2-methylphenyl)piperazinyl-1)propyl) amino)-3(2H)-pyridazinone
Ki=49.3
2-Methyl-5-((4-(4-(2-methoxyphenyl)piperazinyl-1)butyl) amino)-3(2H)-pyridazinone
Ki=5.38
2-Methyl-5-methoxy-4-((2-(4-(2-methoxyphenyl)-piperazinyl-1) ethyl)amino)-3(2H)-pyridazinone
Ki=7.83
4-Chloro-5-((2-(4-(2-methoxyphenyl)piperazinyl-1)ethyl)amino) -3(2H)-pyridazinone
Ki=5.43
6-Chloro-2-methyl-4-((3-(4-(2-methoxyphenyl)piperazinyl-1) propyl)amino)-3(2H)-pyridazinone
Ki=11.0
6-Chloro-2-ethyl-4-((3-(4-(2-methoxyphenyl)piperazinyl-1) propyl)amino)-3(2H)-pyridazinone
Ki=18.0
3-Chloro-4-((4-(4-(2-methoxyphenyl)piperazinyl-1)butyl) amino)-3(2H)-pyridazinone
Ki=3.34
6-Chloro-4-((2- 4-(2-methoxyphenyl)piperazinyl-1)ethyl) amino)-3(2H)-pyridazinone
Ki=12.8
2-Methyl-6-chloro-4-((2-(4-(2-methoxyphenyl)piperazinyl-1) ethyl)amino)-3(2H)-pyridazinone
Ki=5.63
6-Chloro-4-((2-(4-(2-iso-propoxyphenyl)piperazinyl-1)ethyl) amino)-3(2H)-pyridazinone
Ki=10.0
6-Chloro-4-((3-(4-(2-methoxyphenyl)piperazinyl-1)propyl) amino)-3(2H)-pyridazinone
Ki=11.0
6-Chloro-4-((3-(4-(2-methoxy-4-methylphenyl)piperazinyl-1) propyl)amino)-3(2H)-pyridazinone
Ki=7.49
2-Methyl-6-chloro-3-((3-(4-(2-ethoxyphenyl)piperazinyl-1) propyl)amino)-3(2H)-pyridazinone
Ki=6.5
6-Chloro-2-hydroxyethyl-4-((3-(4-(2-methoxyphenyl) piperazinyl-1)propyl)amino)-3(2H)-pyridazinone
Ki=9.6

REFERENCE COMPOUND 6-(3-(4-(2-Methoxyphenyl)piperazinyl-1)propyl)amino)-1,3-dimethyluracil (URAPIDIL)
Ki=110.0

EXAMPLE B

Determination of the affinity of compounds of the formula I for 5-HT-1A receptors.

The affinity of compounds of the general formula I for 5-HT-1A receptors was determined by the method described by H. Gozlan, S. Elmestikawy, L. Pichat, J. Glowinski and M. Hamon in Nature 305, 140–142 (1983). In this method the competitive displacement of tritiated 8-OH-DPAT (8-hydroxy-(di-n-propylamino)-tetralin) on rat brain membranes by the test substances is measured, and the $IC_{50}$ (50% inhibition concentration) is determined as that concentration which brings about a 50% inhibition of the specific binding of tritiated 8-OH-DPAT to 5-HT-1A receptors in rat brain membranes.

The concentration-independent inhibitor constants $K_i$-alpha$_1$ and $K_i$-5HT-1A were determined from the $IC_{50}$ values as stated by Y. Cheng and H. W. Prusoff in Biochem. Pharmacol. 22, 3099–3108 (1973).

The results of these investigations are compiled in the table which follows:

Inhibition constants at 5-HT1A-receptor:
2-Methyl-5-bromo-4-((2-(4-(2-methoxyphenyl)piperazin-1) ethyl)amino)-3(2H)-pyridazinone
Ki=16.2
2-Methyl-4-bromo-5-((2-(4-(2-methoxyphenyl)piperazinyl-1) ethyl)amino)-3(2H)-pyridazinone
Ki=33.6
2-Methyl-5-chloro-4-((2-(4-(2-methoxyphenyl)piperazinyl-1) ethyl)amino)-3(2H)-pyridazinone
Ki=16.6
2-Methyl-4-chloro-5-((2-(4-(2-methoxyphenyl)piperazinyl-1) ethyl)amino)-3(2H)-pyridazinone
Ki=63.2
2-Methyl-4-chloro-5-((3-(4-(2-methoxyphenyl)piperazinyl-1) propyl)amino)-3(2H)-pyridazinone
Ki=50.7
2-Methyl-5-chloro-4-((3-(4-(2-methoxyphenyl)piperazinyl-1) propyl)amino)-3(2H)-pyridazinone
Ki=1.40
2-Methyl-5-chloro-4-((2-(4-phenylpiperazinyl-1)ethyl)amino)-3(2H)-pyridazinone
Ki=519.0
2-Methyl-5-chloro-4-((2-(4-(2-methoxy-5-methylphenyl) piperazinyl-1)ethyl)amino)-3(2H)-pyridazinone
Ki=85.1
2-Methyl-5-chloro-4-((2-(4-(2-methoxy-4-methylphenyl) piperazinyl-1)ethyl)amino)-3(2H)-pyridazinone
Ki=126.0
2-Methyl-5-chloro-4-((2-(4-(3-trifluoromethylphenyl) piperazinyl-1)ethyl)amino-3(2H)-pyridazinone
Ki=8.31
2-Methyl-5-chloro-4-((2-(4-(2-fluorophenyl)piperazinyl-1) ethyl)amino)-3(2H)-pyridazinone
Ki=80.8
2-t-Butyl-5-chloro-4-((2-(4-(2-methoxyphenyl)piperazinyl-1) ethyl)amino)-3(2H)-pyridazinone
Ki=9.45
2-Hydroxyethyl-5-chloro-4-((2-(4-(2-methoxyphenyl)-piperazinyl -1)ethyl)amino)-3(2H)-pyridazinone
Ki=25.6
4-Chloro-5-((2-(4-(2-methoxyphenyl)piperazinyl-1)ethyl)amino) -3(2H)-pyridazinone
Ki=27.0
2-Methyl-4-chloro-5-((2-(4-phenylpiperazinyl-1)ethyl)amino)-3(2H)-pyridazinone
Ki=106.0
2-Methyl-4-chloro-5-((2-(4-(2-methoxy-4-methylphenyl) piperazinyl-1)ethyl)amino)-3(2H)-pyridazinone
Ki=478.0
2-Methyl-4-chloro-5-((2-(4-(2-methoxy-5-methylphenyl) piperazinyl-1)ethyl)amino)-3(2H)-pyridazinone
Ki=510.0
2-Methyl-4-chloro-5-((2-(4-(2-ethoxyphenyl)piperazinyl-1) ethyl)amino)-3(2H)-pyridazinone
Ki=36.8
2-Methyl-4-chloro-5-((2-(4-(3-trifluoromethylphenyl) piperazinyl-1)ethyl)amino-3(2H)-pyridazinone
Ki=28.5
2-Methyl-4-chloro-5-((2-(4-(2-fluorophenyl)piperazinyl-1) ethyl)amino)-3(2H)-pyridazinone
Ki=398.0
2-t-Butyl-4-chloro-5-((2-(4-(2-methoxyphenyl)piperazinyl-1) ethyl)amino)-3(2H)-pyridazinone
Ki=39.4

2-(Dimethylaminoethyl)-4-chloro-5-((2-(4-(2-methoxyphenyl) piperazinyl-1)ethyl)amino)-3(2H)-pyridazinone
Ki=118.0

2-Hydroxyethl-4-chloro-5-((2-(4-(2-methoxyphenyl)-piperazinyl-1-)ethyl)amino-3(2H)-pyridazinone
Ki=86.3

2-Phenyl-4-chloro-5-((2-(4-(2-methoxyphenyl)piperazinyl-1) ethyl)amino)-3(2H)-pyridazinone
Ki=75.8

2-Methyl-5-((2-(4-(2-methoxyphenyl)piperazinyl-1)ethyl) amino)-3(2H)-pyridazinone
Ki=43.6

2-Methyl-4-((2-(4-phenylpiperazinyl-1)ethyl)amino)-3(2H)-pyridazinone
Ki=261.0

2-Methyl-4-(N-ethyl-(2-(4-(2-methoxyphenyl)piperazinyl-1) ethyl)amino)-3(2H)-pyridazinone
Ki=40.7

2-Methyl-4-((2-(4-(2-methoxy-5-methylphenyl)piperazinyl-1) ethyl)amino)-3(2H)-pyridazinone
Ki=186.0

2-Methyl-4-((2-(4-(2-methoxy-4-methylphenyl)piperazinyl-1) ethyl)amino)-3(2H)-pyridazinone
Ki=272.0

2-Methyl-4-((2-(4-(2-hydroxyphenyl)piperazinyl-1)ethyl) amino)-3(2H)-pyridazinone
Ki=36.5

2-Methyl-4-((2-(4-(3-trifluoromethylphenyl)piperazinyl-1) ethyl)amino-3(2H)-pyridazinone
Ki=4.56

2-Hydroxyethyl-4-((2-(4-(2-methoxyphenyl)piperazinyl-1) ethyl)amino-3(2H)-pyridazinone
Ki=18.2

2-Methyl-4-((3-(4-(2-methoxyphenyl)piperazinyl-1)propyl) amino-3(2H)-pyridazinone
Ki=15.9

2-Methyl-5-((2-(4-phenylpiperazinyl-1)ethyl)amino)-3(2H)-pyridazinone
Ki=274.0

2-Methyl-5-((2-(4-(2-methoxy-4-methylphenyl)piperazinyl-1) ethyl)amino)-3(2H)-pyridazinone
Ki=814.0

2-Methyl-5-((2-(4-(2-methoxy-5-methylphenyl)piperazinyl-1) ethyl)amino)-3(2H)-pyridazinone
Ki=523.0

2-Methyl-5-(N-ethyl-(2-(4-(2-methoxyphenyl)piperazinyl-1) ethyl)amino)-3(2H)-pyridazinone
Ki=24.2

2-t-Butyl-5-((2-(4-(2-methoxyphenyl)piperazinyl-1)ethyl) amino)-3(2H)-pyridazinone
Ki=65.8

2-Hydroxyethyl-5-((2-(4-(2-methoxyphenyl)piperazinyl-1) ethyl)amino)-3(2H)-pyridazinone
Ki=55.8

2-Methyl-4-((3-(4-(2-methoxyphenyl)piperazinyl-1)propyl) amino-3(2H)-pyridazinone
Ki=55.3

2-Methyl-5-methoxy-4-((2-(4-(2-methoxyphenyl)-piperazinyl-1) ethyl)amino)-3(2H)-pyridazinone
Ki=90.8

4-Chloro-5-((2-(4-(2-methoxyphenyl)piperazinyl-1)ethyl)amino) -3(2H)-pyridazinone
Ki=27.0

6-Chloro-2-methyl-4-((3-(4-(2-methoxyphenyl)piperazinyl-1) propyl)amino)-3(2H)-pyridazinone
Ki=46.6

2-Methyl-6-chloro-4-[[2-[4-(2-methoxyphenyl)piperazinyl-1]ethyl]amino]-3(2H)-pyridazinone
Ki=28.4

Reference compound:

6-(3-(4-(2-Methoxyphenyl)piperazinyl-1)propyl)amino)-1,3-dimethyluracil (URAPIDIL)
Ki=93.1

We claim:

1. A piperazinylalkyl-3(2H)-pyridazinone of the formula I $$R_1-N \begin{matrix} O \\ \| \\ N \end{matrix} \begin{matrix} R_2 \\ \end{matrix} -N-B-N \begin{matrix} R_8 \\ \end{matrix} \begin{matrix} R_9 \\ \end{matrix} N-Z \quad I$$

in which
$R_1$ represents hydrogen, $C_1$-$C_6$ alkyl, which is unsubstituted or substituted by hydroxyl or by a group $NR_4R_5$, in which $R_4$ and $R_5$ can be identical or different and which represent hydrogen, methyl or ethyl,
$R_2$ and $R_3$ represent hydrogen, halogen, $C_1$-$C_4$ alkyl or $C_1$-$C_4$ alkoxy, where at least one of the radicals $R_2$ or $R_3$ denotes hydrogen,
$R_6$ represents hydrogen or $C_1$-$C_4$ alkyl,
B represents $C_1$-$C_6$ alkylene,
$R_8$ and $R_9$ represent hydrogen or $C_1$-$C_4$ alkyl, and
Z represents phenyl, which is unsubstituted or substituted one or two times by $C_1$-$C_6$ alkoxy, $C_1$-$C_4$ alkyl, trifluoromethyl, halogen or nitro or pyridyl-2 or pharmaceutically acceptable salts thereof.

2. A pharmaceutical composition for the treatment of disturbances of peripheral circulation comprising a piperazinylalkyl-3(2H)-pyridazinone of the formula I $$R_1-N \begin{matrix} O \\ \| \\ N \end{matrix} \begin{matrix} R_2 \\ \end{matrix} -N-B-N \begin{matrix} R_8 \\ \end{matrix} \begin{matrix} R_9 \\ \end{matrix} N-Z \quad I$$

in which
$R_1$ represents hydrogen, $C_1$-$C_6$ alkyl, which is unsubstituted or substituted by hydroxyl or by a group $NR_4R_5$, in which $R_4$ and $R_5$ can be identical or different and which represent hydrogen, methyl or ethyl,
$R_2$ and $R_3$ represent hydrogen, halogen, $C_1$-$C_4$ alkyl or $C_1$-$C_4$ alkoxy, where at least one of the radicals $R_2$ or $R_3$ denotes hydrogen,
$R_6$ represents hydrogen or $C_1$-$C_4$ alkyl,
B represents $C_1$-$C_6$ alkylene,
$R_8$ and $R_9$ represent hydrogen or $C_1$-$C_4$ alkyl, and
Z represents phenyl, which is unsubstituted or substituted one or two times by $C_1$-$C_6$ alkoxy, $C_1$-$C_4$ alkyl, trifluoromethyl, halogen or nitro or pyridyl-2 or pharmaceutically acceptable salts thereof in an amount effective for the treatment of disturbances of peripheral circulation, in combination with a pharmaceutically acceptable carrier.

3. A method for the treatment of disturbances of peripheral circulation, which comprises administering to a patient an effective amount of a pharmaceutical composition for the treatment of such disturbances comprising a piperazinylalkyl-3(2H)-pyridazinone of the formula I

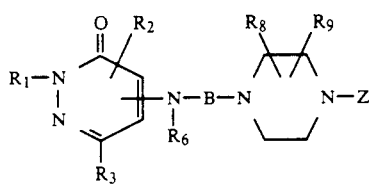

in which
R$_1$ represents hydrogen, C$_1$-C$_6$ alkyl, which is unsubstituted or substituted by hydroxyl or by a group NR$_4$R$_5$, in which R$_4$ and R$_5$ can be identical or different and which represent hydrogen, methyl or ethyl, R$_2$ and R$_3$ represent hydrogen, halogen, C$_1$-C$_4$ alkyl or C$_1$-C$_4$ alkoxy, where at least one of the radicals R$_2$ or R$_3$ denotes hydrogen, R$_6$ represents hydrogen or C$_1$-C$_4$ alkyl, B represents C$_1$-C$_6$ alkylene, R$_8$ and R$_9$ represent hydrogen or C$_1$-C$_4$ alkyl, and Z represents phenyl, which is unsubstituted or substituted one or two times by C$_1$-C$_6$ alkoxy, C$_1$-C$_4$ alkyl, trifluoromethyl, halogen or nitro or pyridyl-2 or pharmaceutically acceptable salts thereof, in combination with a pharmaceutically acceptable carrier.

* * * * *